United States Patent
Fujimoto et al.

[11] Patent Number: 5,177,802
[45] Date of Patent: Jan. 5, 1993

[54] FINGERPRINT INPUT APPARATUS

[75] Inventors: Yoshiji Fujimoto; Masayuki Katagiri, both of Nara; Naoyuki Fukuda, Kita-Katsuragi; Kenji Sakamoto, Nara, all of Japan

[73] Assignee: Sharp Kabushiki Kaisha, Japan

[21] Appl. No.: 663,126

[22] Filed: Mar. 4, 1991

[30] Foreign Application Priority Data

| Mar. 7, 1990 | [JP] | Japan | 2-55666 |
| Aug. 6, 1990 | [JP] | Japan | 2-208694 |
| Sep. 11, 1990 | [JP] | Japan | 2-241725 |
| Nov. 26, 1990 | [JP] | Japan | 2-321713 |
| Jan. 17, 1991 | [JP] | Japan | 3-3942 |

[51] Int. Cl.⁵ .............................................. G06K 9/20
[52] U.S. Cl. ........................................ 382/4; 336/7.1
[58] Field of Search ................ 382/4, 2, 5; 356/71

[56] References Cited

U.S. PATENT DOCUMENTS

| 3,975,711 | 8/1976 | McMahon | 382/4 |
| 4,246,568 | 1/1981 | Peterson | 382/4 |
| 4,569,080 | 2/1986 | Schiller | 382/4 |
| 4,785,171 | 11/1988 | Dowling, Jr. et al. | 382/4 |
| 4,905,293 | 2/1990 | Asai et al. | 382/4 |
| 5,077,803 | 12/1991 | Kato et al. | 382/4 |

FOREIGN PATENT DOCUMENTS 63-156294  6/1988  Japan.

Primary Examiner—Herbert Goldstein
Assistant Examiner—Yon Jung
Attorney, Agent, or Firm—Nixon & Vanderhye

[57] ABSTRACT

A fingerprint input apparatus is constructed to have simple construction. It serves to provide an excellen S/N ratio and reliably input a fingerprint pattern. The fingerprint input apparatus includes a light source for emitting a ray of light, a lightguide plate having a predetermined location at which a finger can be contact with the lightguide plate, a unit for directing the ray of light into at least one surfaces of the lightguide plate in a manner to keep such an angle of incidence as allowing the ray of light to be totally reflected within the lightguide plate, the lightguide plate being constructed to direct the ray of light into the predetermined location, and an image pickup unit located near the predetermined location of the lightside plate and outside of an opposite surface to a surface having the predetermined location, the image pickup unit being constructed to pick up a right irregularly reflected on a fingerprint surface of the finger contacted with the predetermined location.

22 Claims, 30 Drawing Sheets

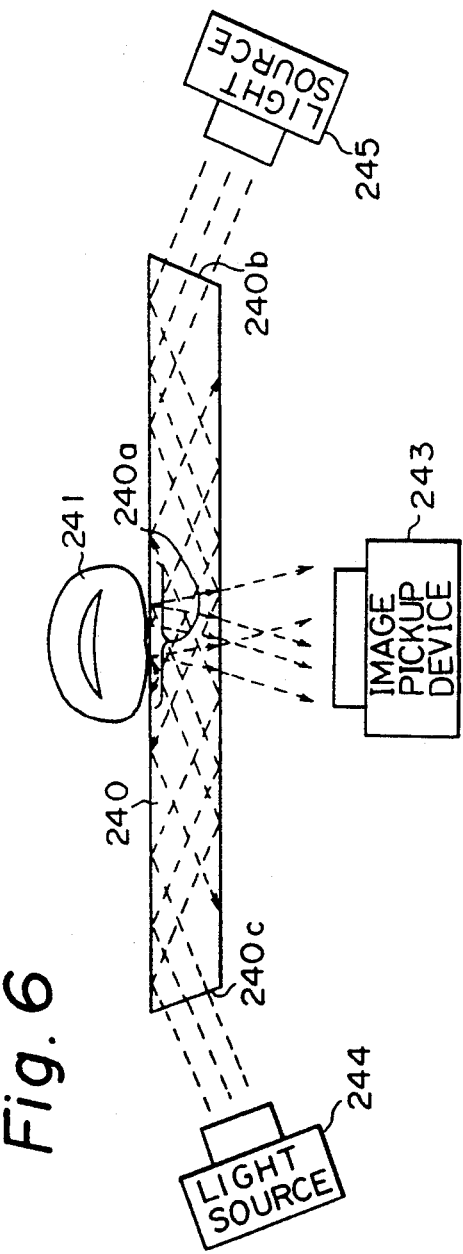
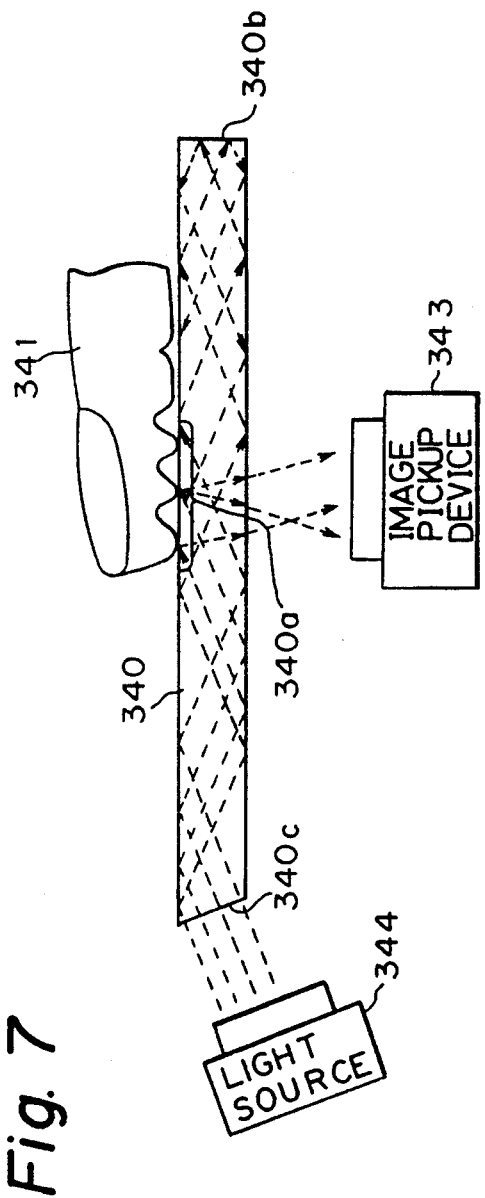

Fig. 21A
Fig. 21B
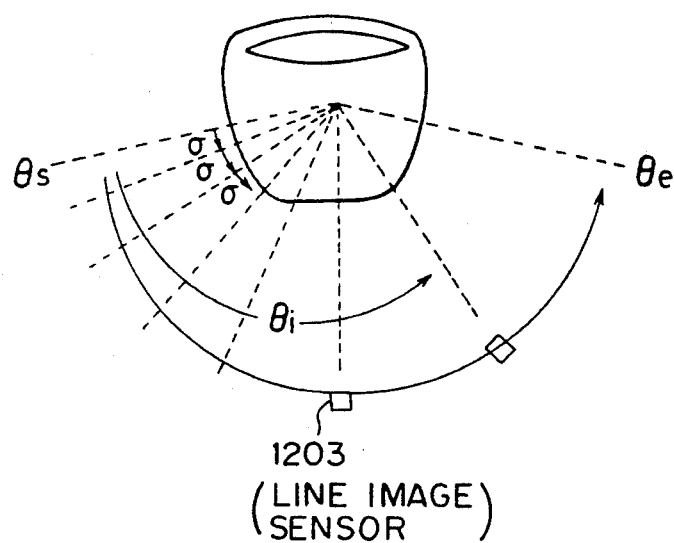
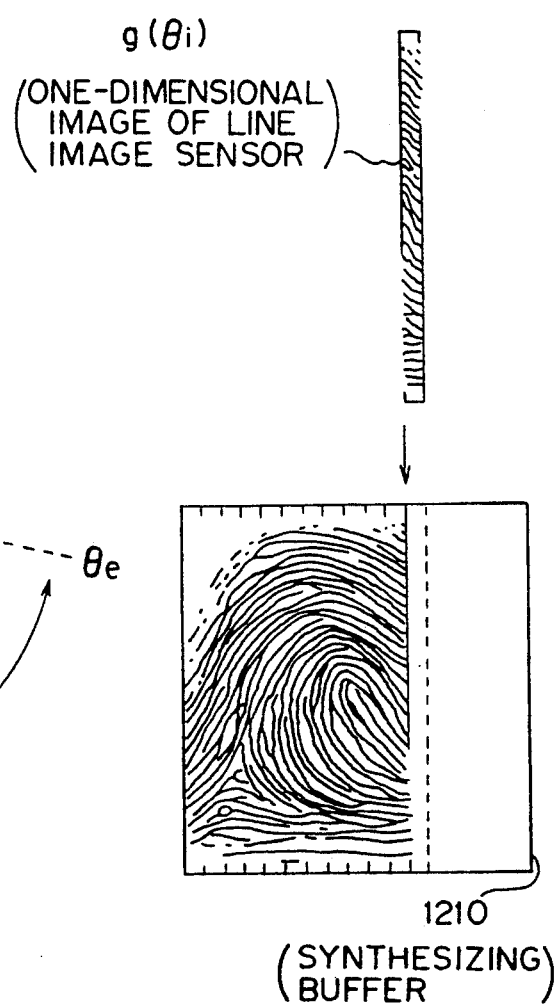

FINGERPRINT INPUT APPARATUS

BACKGROUND OF THE INVENTION

1. Field of the Invention

The present invention relates to a fingerprint input apparatus which is suitable for fingerprint collation or identification.

2. Description of the Related Art

For obtaining a fingerprint as means for identifying each person, it is preferably to use a non-ink type data input apparatus which gives less mental and physical burden to a user. Further, as a result of considering the post-processing of an image, the fingerprint input apparatus is required to obtain the image on which ridges and valleys are displayed at high contrast and provide 50 μm or some reading accuracy per one pixel.

The inventors of the present invention know two types of fingerprint input apparatus, the type employing the steps of applying a laser beam to materials contained in skin secretion and sensing light reflected on the materials and the type employing the steps of applying a ray of light to one surface of a glass plate on the other surface with which a finger is in contact and sensing a variation of the reflected light (see "Fingerprint Automatic Identifying Technique" KAWAGOE Masahiro, Measurement and Control, Vol. 25 No. 8 pp. 701-706). The commonly used fingerprint input apparatus employs "a prism method" relevant to the latter type. The prism method takes the steps of applying a ray of light to an oblique surface of a prism from the inside in a manner to allow the light to be totally reflected and image-form the regular reflected light from the inside of the prism on an image pickup device provided in an image-form optical system. When inputting a fingerprint image, a finger is required to be pushed on the oblique surface so that the convex portions of the fingerprint cause the ray of light to be scattered so that the ray of light is not allowed to reach the image pickup device, since the skin is in contact with the glass at the convex portions. This principle makes it possible to obtain a high-contrast fingerprint image. (see "Automatic Identifying a fingerprint pattern", written by KAWAGOE and TOHJYO, Proceeding on Information Processing Society, Computer Vision, 18-2, 1982)

Another method has been proposed wherein an image pickup device is located at the area on which no scattered light from the recessed portions of the fingerprint is allowed to reach for the purpose of improving a contrast (see "Method for detecting fingerprint information using a prism, written by SHIMIZU et al., National Meeting of Electronics and Communication Society, 1311, 1984).

The aforementioned methods have the following disadvantages.

(1) Appearance of a trapezoidal distortion resulting from various light paths from respective points on the fingerprint to the image pickup device, (2) Overlapping of "Noise light" resulting from a residual fingerprint of a previous user, and (3) Inability to reduce the overall system in size, resulting from the essential requirement of an optical system for forming an image on the outside of the prism.

Further, another fingerprint input apparatus has been proposed wherein a hologram is provided for inputting a two-dimensional image representing ridge portions of a fingerprint. This is devised for overcoming the adverse effect caused by the residual fingerprint (see "Personal Collation Device Using Holographic Fingerprint Sensor", written by IGAKI et al., Proceeding on Electronic, Information and Communication Society, Pattern Recognition and Understanding 88-38, 1988).

The aforementioned fingerprint input apparatus, however, each provides means having a glass plate with which a finger is in contact. Hence, it may leave the residual fingerprint on the glass plate, which results in bringing about noise light. The overlapping of the noise light with the light to be imaged thus makes it difficult to draw the features of the fingerprint. If the prism is used for the surface with which a finger is in contact, the trapezoidal distortion takes place because various light paths are provided between respective points on the fingerprint and the image pickup device. If the finger is even a bit slipped, the trapezoidal distortion may cause the fingerprint image to be further distorted. Moreover, since each person has each moisture on his finger, some fingerprints may be represented as a dim image. The inventors of the present invention know the use of a two-dimensional image sensor for directly imaging the fingerprint surface. This method, however, requires uniform lighting on the overall fingerprint for obtaining a uniform fingerprint image. If not, the uniform fingerprint image is not allowed to be obtained, resulting in improperly collating fingerprints. Further, the use of the two-dimensional image sensor enhances the cost of the apparatus.

As another fingerprint apparatus, the inventors of the present invention know that a non-contact type fingerprint apparatus is provided for overcoming the foregoing disadvantages. The non-contact type fingerprint apparatus is constructed so that a user does not need to contact his or her finger on a glass plate or the like for inputting the fingerprint. However, the non-contact fingerprint apparatus is incapable of precisely inputting a fingerprint pattern, because the non-contact feature makes it substantially impossible to contact the finger in stable form. This apparatus, therefore, has a significant problem that the positional, directional and rotational slippage of the fingerprint surface has to be reduced.

In turn, more concrete description about the aforementioned known arts will be made.

As the first related art, a fingerprint input apparatus includes a prism whose section is formed like a right-angled isosceles triangle, a light source, and an image pickup device. In operation, someone pushes his or her finger on a bottom of the prism located in opposition to the right-angled vertex. The light source applies a ray of light to the opposite side of the finger-put bottom of the prism at the 45° angle of incidence. The finger image representing finger contour is reflected on the bottom and comes to the image pickup device. The image pickup device is located at 45° angle against the bottom of the prism and picks up the finger image reflected from the bottom. The finger image is converted into an electric signal in the image pickup device.

As the second related art, the fingerprint input apparatus includes a prism whose section is formed like a right-angled isosceles triangle, a light source, and an image pickup device as well. In operation, someone pushes his or her finger on a bottom of the prism located in opposition to the right-angled vertex. The light source applies a ray of light to the opposite side of the finger-put bottom of the prism in a manner to keep the angle of incidence larger than a critical angle relevant to the total internal reflection of the bottom. The critical angle is used herein to denote a minimum angle against a vertical plane of the prism bottom which brings about total internal reflection. The contour of the fingerprint causes a ray of light to be irregularly reflected on the bottom. The irregularly reflected light is picked up by the image pickup device located on the same side of the light source but at the closer position than the light source. The image pickup device converts the light into an electric signal. The portions of the bottom on which the finger does not closely contact causes the ray of light to be totally reflected and come out of the prism.

As the third related art, the fingerprint input apparatus includes a lightguide plate having a hologram attached on one surface and made of glass, for example, a laser beam source for emitting a coherent laser beam, and an image pickup device. In operation, someone pushes his or her finger on a part of one surface of the lightguide plate. The laser beam source applies the coherent laser beam to the finger-put area of the surface. The contour of the fingerprint causes the coherent laser beam to be irregularly reflected. The irregularly reflected light is propagated within the light guide plate and reaches the hologram attached on the opposite surface of the finger-put surface of the lightguide plate. The hologram picks up the irregularly reflected light from the lightguide plate and applies the light to the image pickup device. The image pickup device converts the light into an electric signal. The laser beam comes out of the lightguide plate on the portions of the surface on which the finger does not closely contact, that is, the portions corresponding to the concaves of the fingerprint. It is reflected on the concaves of the fingerprint and returned into the lightguide plate. The light is, however, got out of the opposite surface of the lightguide plate, so that it does not reach the hologram.

The fingerprint input apparatus according to the first related art has an advantage that it has simple construction. However, the apparatus has a disadvantage that the image reflected on the contour of the fingerprint has a very low S/N (Signal-to-Noise) ratio, because the angle of incidence of the light against the bottom is as small as 45°.

The construction of the fingerprint input apparatus according to the second related art results in that the non-contact portions on the bottom between the contour of the fingerprint and the prism causes the ray of light to be totally reflected and outgo from the bottom of the prism without being irregularly reflected. It means that no light reflected from the non-contact portions is allowed to reach the image pickup device. The second related art is capable of providing a somewhat higher S/N ratio than the first related art. It, however, cannot sufficiently improve the S/N ratio in light of the fact that a slight quantity of irregularly-reflected light is allowed to reach the image pickup device.

The construction of the fingerprint input apparatus according to the third related art results in that the non-contact portions on the surface between the contour of the fingerprint and the lightguide plate cause the incident ray of light to outgo from the lightguide plate without allowing the light to reach the hologram. Hence, the third related art is capable of providing a far more excellent S/N ratio than the foregoing related arts. However, the disadvantage the third related art entails is the high manufacturing cost, because the third related art needs a dedicated laser beam source and optical devices such as a hologram.

SUMMARY OF THE INVENTION

It is, therefore, a first object of the present invention to provide a fingerprint input apparatus which is capable of providing an excellent S/N ratio and being made inexpensively.

It is a second object of the present invention to provide a fingerprint input apparatus which is capable of directly imaging ridge portions and recess portions of a fingerprint by using a one-dimensional line image sensor without having to contact a finger on a glass surface or the like and inputting a precise fingerprint image with no adverse effect caused by the residual fingerprint and irregular lightning.

It is a third object of the present invention to provide a fingerprint input apparatus which is capable of reliably inputting a fingerprint pattern without adverse effect of the residual fingerprint and provides simple construction.

It is a fourth object of the present invention to provide a fingerprint input apparatus which is capable of reliably inputting a fingerprint pattern without adverse effect of the residual fingerprint and provides non-contact type simple construction.

In carrying out the objects in a preferred mode, the present invention provides a fingerprint input apparatus which includes;

a lightguide plate having a predetermined location at which a finger can be contact with the lightguide plate, a light source for emitting a ray of light, means for directing the ray of light into a least one surfaces of the lightguide plate in a manner to keep such an angle of incidence as allowing the ray of light to be totally reflected within the lightguide plate, and an image pickup means located near the predetermined location of the lightguide plate and outside of an opposite surface to a surface having the predetermined location, wherein the lightguide plate is constructed to direct the incident ray of light into the predetermined location, and the image pickup means is constructed to pick up the right irregularly reflected on a fingerprint surface of the finger contacted with the predetermined location.

The second invention provides a fingerprint input apparatus which includes;

a lightguide plate having a through hole on which a finger is placed, at least one light sources for emitting a ray of light, means for directing the ray of light into at least one surface of the lightguide plate in a manner to keep such an angle of incidence as allowing the ray of light to be totally reflected within the lightguide plate, and an image pickup means located in opposition to the finger through the through hole therebetween, wherein the lightguide plate is constructed to direct the incident ray of light out of the end surface of the through hole and into the finger, and the image pickup means is constructed to pick up a right irregularly reflected on a fingerprint surface of the finger.

In the operation of the first invention, the light source applies a ray of light to the lightguide plate at such an angle of incidence as allowing the light to be totally reflected within the lightguide plate. The incident light propagates through the lightguide plate as repeating the total reflection and reaches the portion with which a finger is in contact. Depending on the contour of the fingerprint, the light is irregularly reflected on the portion where the finger surface actually contacts and totally reflected on the portion where the finger surface does not contact. The totally reflected light is further propagated within the lightguide plate. The irregularly reflected light is picked up by the image pickup means located nearby the finger-contact portion and outside of the opposite surface to the finger-contact surface. Then the image pickup means serves to convert the light into an electric signal representing a fingerprint pattern.

In the operation of the second invention, the ray of light is incident to the lightguide plate at such an angle of incidence as allowing the light to be totally reflected. The incident light propagates through the lightguide plate as repeating the total reflection. The lightguide plate provides a hole formed on the portion on which a finger is to be placed. The propagated light outgoes from the hole to the finger. Depending on the contour of the fingerprint, the light is reflected from the finger surface and is picked up by the image pickup means located in opposition to the finger through the hole located between the finger and the image pickup means itself. Then, the image pickup means serves to convert the light into an electric signal representing the fingerprint.

Further, the third invention provides a fingerprint input apparatus which includes;
a finger guide for guiding a finger to a predetermined location,
an opening window formed on the predetermined location of the finger guide,
at least one two-dimensional image sensors provided to focus on the predetermined location, and
a light source for applying a ray of light to the predetermined location through the opening window,
wherein the fingerprint input apparatus is constructed so that ridges and valleys formed on a fingerprint surface of the finger are directly imaged without contacting the fingerprint surface with anywhere.

In operation, the finger is guided to a predetermined place along a finger guide. With the image pickup starting switch being turned on, the fingerprint is image-formed on the two-dimensional image sensor through the window. Then, the two-dimensional image sensor serves to input an image representing the fingerprint. As alternative means, the image pickup starting switch may be provided to be turned on by the tip of the finger inserted through the finger guide. In this case, it is only necessary to guide the finger tip to a predetermined place along the finger guide for the purpose of allowing the fingerprint image to be input without having to place the finger on the glass or the like.

The fourth invention provides a fingerprint input apparatus which includes;
a finger guide having a guide portion for guiding a finger to a predetermined location and an opening window formed on the predetermined location,
a one-dimensional line image sensor provided to focus on the predetermined location,
a lighting device for lighting up the predetermined location,
a driving means for moving the one-dimensional line image sensor and the lighting device in concert,
a movement sensing means for sensing a movement of the one-dimensional line sensor, and
a fingerprint input control means for imaging one-dimensional images based on an output signal of the moving sensing means and synthesizing the one-dimensional images into a two-dimensional image, wherein the fingerprint input apparatus is constructed so that ridges and valleys of a fingerprint surface of the finger are directly imaged without contacting the fingerprint surface with anywhere.

In operation, the finger tip is guided to a predetermined place along the finger guide. With the image pickup starting switch being turned on, a part of the fingerprint is image-formed on the one-dimensional line image sensor through the window without having to place the finger on the glass or the like. Then, the one-dimensional line image sensor and the lighting device are moved in concert so that the one-dimensional image with uniform luminous is sequentially read. The synthesizing of the sequentially read images produces a two-dimensional fingerprint image.

The one-dimensional line image sensor and the lighting device are allowed to move in curved manner along the fingerprint surface for the purpose of inputting the fingerprint located on the sides of the finger.

Further, the image pickup starting switch may be provided at the bottom of the finger guide so that the image pickup starting switch is turned on by the tip of the finger inserted through the finger guide.

The fifth invention provides a fingerprint input apparatus which includes;
a lighting means for lighting up a finger,
a roller located in the direction perpendicular to the movement of the finger and allowed to rotate by the movement of the finger contacting the roller,
a movement sensing means for sensing movement of the finger on the basis of the rotation of the roller,
a one-dimensional image pickup means for directly receiving a light reflected on a fingerprint surface of the finger and picking up a one-dimensional image formed perpendicular to the movement of the finger, and
a synthesizing means for synthesizing a two-dimensional image of a fingerprint pattern on the basis of the one-dimensional image picked up by the one-dimensional image pickup means and the movement of the finger sensed by the movement sensing means.

The sixth invention provides a fingerprint input apparatus which includes;
a lighting means for lighting up a subject finger,
a guide means for accommodating the subject finger,
a movement sensing means for sensing movement of the finger,
a one-dimensional image pickup means for directly receiving the light reflected on a fingerprint surface of the finger and picking up one-dimensional images formed perpendicular to a movement of the finger, and
a synthesizing means for synthesizing a two-dimensional image of a fingerprint pattern on the basis of the one-dimensional images picked up by the one-dimensional imaging means and the movement of the finger sensed by the movement sensing means.

In the operation of the fifth invention, the lighting means serves to light a finger. As the finger moves in contact with the roller, the roller is rotated. The movement sensing means serves to sense the movement of the finger based on the rotation of the roller. The light reflected on the finger is directly picked up by the one-dimensional image pickup means so that the one-dimensional image pickup means enables to image the one-dimensional image formed in the direction perpendicular to the moving direction of the finger. The synthesizing means serves to synthesize a two-dimensional image of a fingerprint pattern on the basis of the one-dimensional image picked up by the one-dimensional image pickup means and the movement of the finger sensed by the movement sensing means. The simple construction, therefore, makes it possible to positively input the fingerprint pattern without any adverse effect of the residual fingerprint.

In the operation of the sixth invention, the finger is inserted inside of the guide means and is guided along the guiding means. The movement sensing means serves to sense the movement of the finger. The inserted finger is being lit by the lighting means. The light reflected on the finger is directly picked up by the one-dimensional image pickup means so that the one-dimensional image pickup means enables to image the one-dimensional image formed in the direction perpendicular to the moving direction of the finger. The synthesizing means serves to synthesize the two-dimensional image on the basis of the one-dimensional image picked up by the one-dimensional image pickup means and the movement of the finger sensed by the movement sensing means. The simple construction, therefore, makes it possible to reliably input the fingerprint pattern without any adverse effect of the residual fingerprint as well.

The seventh invention provides a fingerprint input apparatus which includes;

a supporting plate along which two or more fingers can move, for supporting the two or more fingers, a guide means standing upright on the supporting plate and for guiding a finger of the two or more fingers as being clipped by the finger and another finger adjacent to the finger, an image pickup means located as opposed to a fingerprint surface of the finger guided by the guide means and for picking up a fingerprint pattern of the finger surface, and a sensing control means for sensing whether or not the finger guided by the guide means is located at a predetermined location and actuating the image pickup means if the finger is at the location.

The finger and the adjacent finger are moved along the guiding means in a manner to locate the guiding means between both fingers. The sensing control means serves to control the image pickup means in a manner that the image pickup means enables to pick up the fingerprint pattern when the control means senses the finger is located at the predetermined place. Hence, the fingerprint pattern is directly picked up by the image pickup means without having to contact the finger on the supporting plate. Since the fingers are located on both sides of the guiding means when they are moving, it is positive and easy to position the image representing the fingerprint pattern. The simple construction, therefore, makes it possible to reliably input the fingerprint pattern without any adverse effect of the residual fingerprint.

Further objects and advantages of the present invention will be apparent from the following description of the preferred embodiments of the invention as illustrated in the accompanying drawings.

BRIEF DESCRIPTION OF THE DRAWINGS

FIG. 6 is a side view schematically showing construction of a fingerprint input apparatus according to a third embodiment of the first invention;

FIG. 7 is a side view schematically showing construction of a fingerprint input apparatus according to a fourth embodiment of the first invention;

FIG. 21A is a view showing relation between rotation of an image sensor and a finger tip according to the first embodiment of the fourth invention;

FIG. 21B is a view showing how a two-dimensional fingerprint image is synthesized by a one-dimensional image transferred to a synthesizing buffer according to the first embodiment of the fourth invention;

DESCRIPTION OF THE PREFERRED EMBODIMENTS

Before describing the preferred embodiments of the invention, the representative three related arts will be described for easier and deeper understanding of the present invention.

Figure 1:
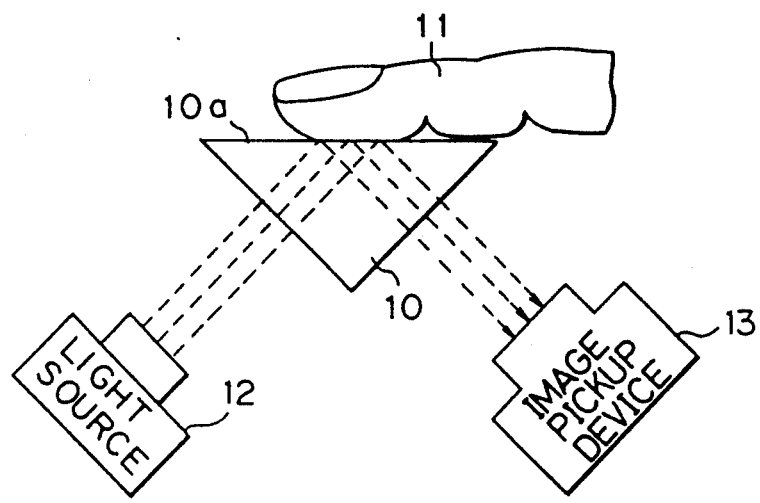
FIGS. 1 to 3 are side views showing a fingerprint input apparatus according to the related art of the present invention.

In FIG. 1, 10 denotes a prism whose section is formed a right-angled isosceles triangle. Someone pushes his or her finger 11 on a prism surface 10a of the prism located in opposition to the right-angled vertex. Reference numeral 12 denotes a light source which applies a ray of light to the opposite side of the fingerplaced prism surface 10a of the prism 10 at the 45° angle of incidence. The finger image representing a fingerprint contour is reflected from the prism surface 10a and comes to an image pickup device 13. The image pickup device 13 is located at 45° angle to the prism surface 10a of the prism 10 and picks up the fingerprint image reflected from the prism surface 10a. The fingerprint image is converted into an electric signal in the image pickup device 13.

Figure 2:
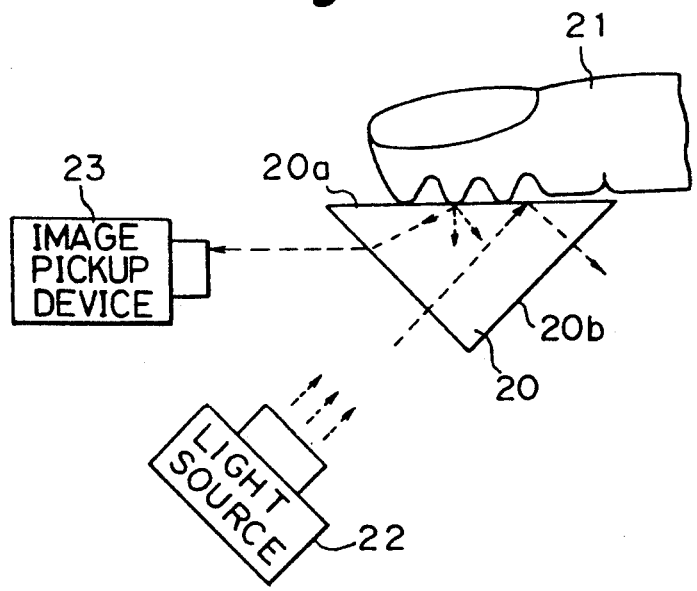

FIG. 2 shows another related art of the present invention. This related art includes a prism 10, a light source 12, and an image pickup device 13 as shown in FIG. 2. The prism has a section formed like a right-angled isosceles triangle. Someone pushes his or her finger 21 on a prism surface 20a of the prism 20 located in opposition to the right-angled vertex. The light source 22 applies a ray of light to the opposite side of the finger-placed prism surface 20a of the prism in a manner to keep the angle of incidence larger than a critical angle relevant to the total internal reflection of the bottom. The contour of the fingerprint causes a ray of light to be irregularly reflected on the prism surface 20a. The irregularly reflected light is picked up by an image pickup device 23 located on the same side of the light source 22 but at the closer position than the light source 22. The image pickup device 23 converts the light into an electric signal. The portions of the prism surface 10a on which the finger 21 does not contact cause the ray of light to be totally reflected and exits from the prism.

Figure 3:
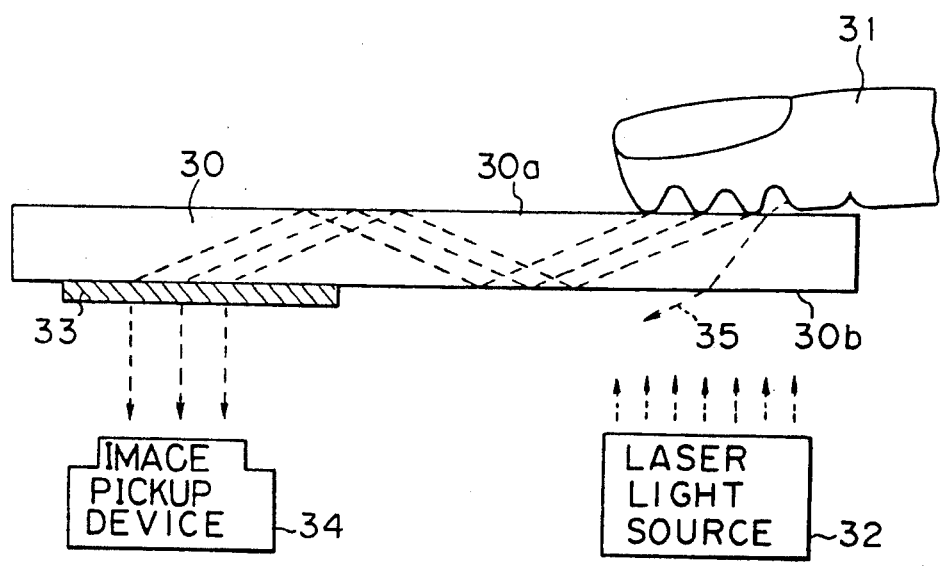

FIG. 3 shows the other related art of the present invention. This related art includes a lightguide plate 30 having a hologram 33 attached on one surface and made of glass, for example, a laser beam source 32 for emitting a coherent laser beam, and an image pickup device 34. Someone contacts his or her finger 31 on a part of one surface 30a of the lightguide plate 30. The laser beam source 32 applies the coherent laser beam to the finger-placed area of the surface. The contour of the fingerprint causes the coherent laser beam to be irregularly reflected. The irregularly reflected light is propagated within the light guide plate 30 and reaches the hologram 33 attached on the opposite surface 30b of the finger-put surface of the lightguide plate 30. The hologram 33 picks up the irregularly reflected light from the lightguide plate 30 and applies the light to the image pickup device 34. The image pickup device 34 converts the light into an electric signal. The laser beam exits from the lightguide plate 30 on the portions of the surface on which the finger 31 does not contact, that is, the portions corresponding to the concaves of the fingerprint. It is reflected on the concaves of the fingerprint and returned into the lightguide plate 30. The light which exits the opposite surface 30b of the lightguide plate 30 does not reach the hologram 33.

The fingerprint input apparatus shown in FIG. 1 has an advantage that it has simple construction. However, the apparatus has a disadvantage that the image reflected on the contour of the fingerprint has a very low S/N ratio, because the angle of incidence of the light against the prism surface 10a is as small as 45°.

The construction of the fingerprint input apparatus shown in FIG. 2 results in that the non-contact portions on the prism surface 20a between the contour of the fingerprint and the prism causes the ray of light to be totally reflected and outgo from the bottom 20a of the prism without being irregularly reflected. It means that no light reflected from the non-contact portions is allowed to reach the image pickup device 23. The related art shown in FIG. 2 is capable of providing a somewhat higher S/N ratio than the related art shown in FIG. 1. It, however, cannot sufficiently improve the S/N ratio in light of the fact that a slight quantity of irregularly-reflected light is allowed to reach the image pickup device 23.

The construction of the fingerprint input apparatus shown in FIG. 3 results in that the non-contact portions on the surface between the contour of the fingerprint and the lightguide plate 30 cause the incident ray of light to exit from the lightguide plate 30 without allowing the light to reach the hologram 33. Hence, this related art is capable of providing a far more excellent S/N ratio than the foregoing related arts. However, the disadvantage this related art entails is the high manufacturing cost, because this related art needs a dedicated laser beam source 32 and optical devices such as a hologram 33.

Next, the description will be directed to a first embodiment of the first invention.

Figure 4:
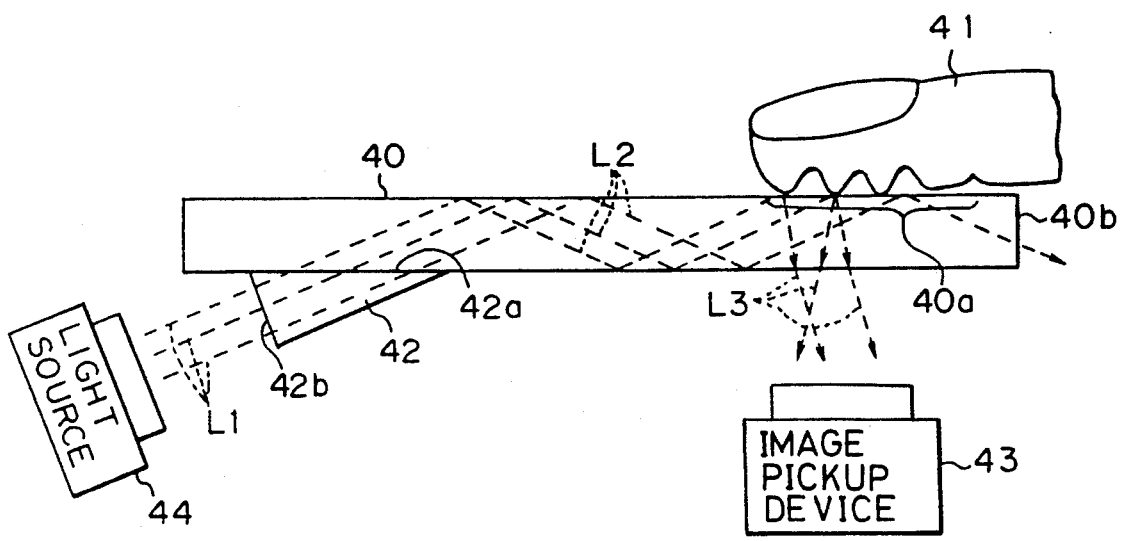
FIG. 4 is a side view schematically showing construction of a fingerprint input apparatus according to a first embodiment of the first invention.

FIG. 4 is a side view schematically showing the construction of a first embodiment of the first invention.

As shown in FIG. 4, 40 denotes a transparent lightguide plate located horizontally. The light guide plate 40 is made of a band-like glass plate, for example. The lightguide plate 40 provides on the upper-right (viewed in FIG. 4) side a fingerprint pick-up portion 40a with which a finger 41 is in contact.

The lightguide plate 40 has dimensions of about 100 mm and 30 to 40 mm, the 100-mm dimension of which corresponds to the light-propagating direction (horizontal direction as viewed in FIG. 4). The length extending in the light-propagating direction is made far longer than the length of the fingerprint pick-up portion 40a (10 to 20 mm).

Reference numeral 42 denotes a prism attached on the lower-left surface (viewed in FIG. 4) against the fingerprint pick-up portion 40a of the lightguide plate 40. The prism 42 has a section formed like a right-angled isosceles triangle. The prism 42 is attached on the lightguide plate 40 in a manner to locate a bottom 42a opposed to a right-angled vertex in contact with the lightguide plate 40. The adhesive agent used for attaching has the same index of refraction as the lightguide plate 40. The prism 42 may be attached on the upper-left surface against the fingerprint pick-up portion 40a.

Reference numeral 43 denotes an image pickup device provided right below the fingerprint pick-up portion 40a of the lightguide plate 40. As shown, a light source 44 is provided in opposition to one surface 42b of the prism 42. The light source 44 applies a ray of light L1 to the prism 42 through which the ray of light is entered to the lightguide plate 40. An angle of incidence against the lightguide plate 40 is set slightly larger than a critical angle causing total internal reflection in the lightguide plate 40 (in general, the critical angle of the glass is about 41.2 degrees). For setting the angle of incidence, it is possible to adjust the form of the prism 42 and the position and the emitting direction of the light source 44.

It is preferable that the light source 44 emits parallel rays of light L1, though complete parallel rays are not required. This is because if the ray of light is entered into the lightguide plate 40 at a smaller angle of incidence than the critical angle relevant to the total internal reflection of the lightguide plate 40, the light passes through the upper surface or the lower surface to the external of the lightguide plate 40 without being propagated within the lightguide plate 40.

If the ray of light is entered to the lightguide plate 40 at a larger angle of incidence than the critical angle relevant to the total internal reflection of the lightguide plate 40, the ray of light L2 is propagated within the lightguide plate 40 as repeating the total internal reflections on the upper surface and the lower surface of the lightguide plate 40 and reaches the fingerprint pick-up portion 40a.

When the finger 41 is not in contact with the fingerprint pick-up portion 40a located on the upper surface of the lightguide plate 40, the ray of light L2 is totally reflected on the fingerprint pick-up portion 40a and exits from the right-hand end 40b (as viewed in FIG. 4). Hence, no light is allowed to reach the image pickup device 43.

When the finger 41 is in contact with the fingerprint pick-up portion 40a, irregular reflection is brought about on the ridges of the fingerprint pattern contacting with the upper surface of the lightguide plate 40. The ray of light L3 is reflected from the ridges of the fingerprint pattern at a smaller angle than the critical angle relevant to the total internal reflection and exits from the lower surface of the lightguide plate 40, finally reaching the image pickup device 43. The image pickup device 43 serves to focus the ray of light L3 for forming an image and converts the focused light into an electric signal. It results in being able to obtain the electric signal representing the fingerprint pattern.

Figure 5:
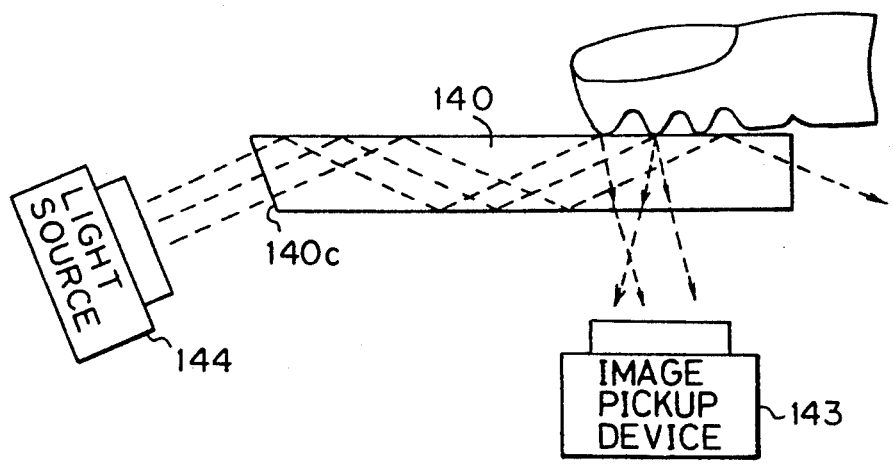
FIG. 5 is a side view schematically showing construction of a fingerprint input apparatus according to a second embodiment of the first invention.

FIG. 5 is a side view schematically showing construction of a second embodiment of the first invention.

The second embodiment is basically likewise to the embodiment shown in FIG. 4, except that a light source 144 applies a ray of light to an end of a lightguide plate 140 rather than through the prism.

The second embodiment includes the light source 144, the lightguide plate 140, and an image pickup device 143. It is thus advantageous in light of the simple construction.

The end 140c of the lightguide plate 140 may be constructed to be located at right angles with the upper surface and the lower surface of the lightguide plate 140. For maximizing the incidence efficiency, it is better to locate the end 140c at such angles with those surfaces as shown in FIG. 5 and the light source 14 applies the ray of light perpendicularly to the end 140c.

FIG. 6 is a side view schematically showing a third embodiment of the first invention.

This third embodiment is basically likewise to the second embodiment shown in FIG. 5, except that a fingerprint pick-up portion 240a is located on the center of a lightguide plate 240 and a ray of light is entered from the right and the left end of the lightguide plate 240.

Light sources 244 and 245 are provided on the right and the left sides of the lightguide plate 240. The light sources 244 and 245 respectively apply a ray of light to the lightguide plate 240 through the ends 240c and 240b. The rays of light emitted from both of the light sources 244 and 245 are applied to the fingerprint pick-up portion 240a.

This third embodiment makes it possible to double the quantity of light irregularly reflected on the ridges of the fingerprint pattern and applied to an image pickup device 243 and reduce shading caused on the fingerprint pattern image, resulting in greatly improving the S/N ratio.

FIG. 7 is a side view schematically showing construction of a fourth embodiment of the first invention.

This fourth embodiment is basically likewise to the second embodiment shown in FIG. 5, except that the three surfaces, that is, two sides and one end surface 340b are made of mirrors on which metal such as aluminium is vaporized.

According to the fourth embodiment, the ray of light emitted by a light source 344 is propagated within a lightguide plate 340 as being positively reflected on the two side surfaces and the end surface 340b and reaches the fingerprint pick-up portion 340a. Like the third embodiment shown in FIG. 6, this fourth embodiment makes it possible to greatly increase the quantity of light irregularly reflected on the ridges of the fingerprint pattern and applied to an image pickup device 343 and reduce shading caused on the fingerprint pattern image, resulting in being able to greatly enhance the S/N ratio. Besides, the present embodiment provides just one light source unlike the third embodiment shown in FIG. 6. Hence, the manufacturing cost is lower.

As set forth above, the first invention including the forgoing first to fourth embodiments basically includes the light source, the lightguide plate, and the image pickup device. Hence, it can provides a very small and inexpensive fingerprint input apparatus. Further, the first invention is constructed so that the image pickup device is allowed to receive all the rays of light reflected on the portions contacting with the ridges of the fingerprint pattern at a smaller angle of incidence than the critical angle relevant to the total internal reflection and form an image. It results in being able to greatly enhance the S/N ratio.

Figure 8:
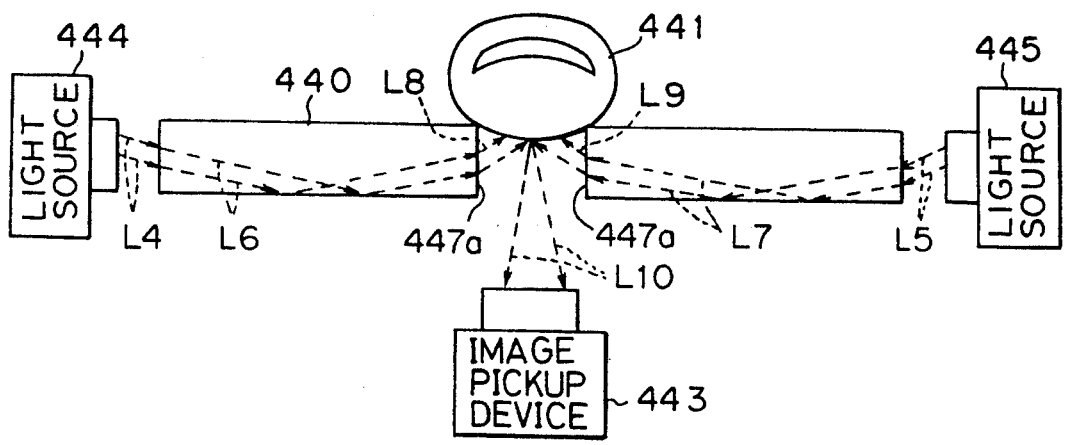
FIG. 8 is a side view schematically showing construction of a fingerprint input apparatus according to a first embodiment of the second invention.
Figure 9:
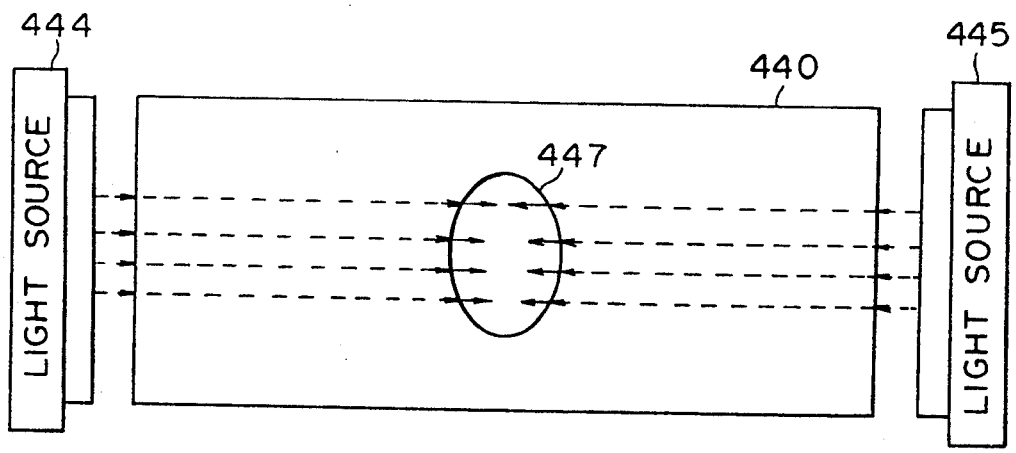
FIG. 9 is a plane view showing the fingerprint input apparatus shown in FIG. 8.

FIG. 8 is a side view schematically showing a first embodiment of the second invention. FIG. 9 is a plane view showing the first embodiment.

As shown in FIGS. 8 and 9, 440 denotes a transparent lightguide plate located in a horizontal manner. The lightguide plate 440 uses a square glass plate, for example. On the center of the lightguide plate 440 is provided a through hole 447 for picking up a fingerprint. A finger 441 is put on an opening of the through hole 447. The through hole 447 has an oval section and a smaller diameter than the size of the finger 441. When actually picking up a fingerprint pattern, with its fingerprint being directed downward, the finger 441 is pushed on the opening of the through hole 447 in a manner to close the opening.

The lightguide plate 440 has dimensions of about 100 mm and 50 mm, the 100-mm dimension of which corresponds to the light-propagating direction (horizontal direction as viewed in FIG. 8). The length extending in the light-propagating direction is made far longer than the length (10 to 20 mm) of the through hole 447 for picking up the fingerprint.

An image pickup device 443 is provided right below the through hole 447 of the lightguide plate 440.

Light sources 444 and 445 are respectively provided on the right and the left sides of the lightguide plate 440. The rays of light emitted from the light sources 444 and 445 are perpendicularly applied to the end surfaces 440c and 440b and are entered into the lightguide plate 440.

The angle of incidence against the lightguide plate 440 is set slightly larger than the critical angle relevant to the total internal reflection of the lightguide plate 440. For reference, the critical angle of commonly used glass is about 41.2 degrees.

It is preferable that the light sources 444 and 445 emit parallel rays of light L4 and L5, though complete parallel rays are not required. This is because if the ray of light is entered into the lightguide plate 440 at a smaller angle of incidence than the critical angle relevant to the total internal reflection of the lightguide plate 440, the light passes through the upper surface or the lower surface to the external of the lightguide plate 440 without being propagated within the lightguide plate 40.

The rays of light L6 and L7 entered into the lightguide plate 440 at a larger angle than the critical angle relative to the total internal reflection are propagated as being totally reflected on the upper and lower surfaces of the lightguide plate 440 and reach the through hole 447 for picking up the fingerprint. Then, the rays of light L6 and L7 exit from an end surface 447a of the through hole 447 into the inside of the through hole 447.

With the fingerprint being directed downwardly, the finger 441 is pushed on the through hole 447 in a manner to close it. Hence, the rays of light L8 and L9 are applied to the fingerprint surface at low angles of incidence. The rays of light L8 and L9 are reflected on the contour of the fingerprint pattern and reach the image pickup device 443. The image pickup device 443 serves to focus the ray of light L10, form an image, and convert the light image into an electric signal. This results in being able to obtain an electric signal representing a fingerprint pattern.

According to the first embodiment of the second invention, the rays of light are applied from both sides of the lightguide plate 440 so that the fingerprint surface is lit from both sides. It results in greatly increasing the quantity of light applied to the image pickup device 443, thereby greatly enhancing the S/N ratio and reducing shading caused on the fingerprint pattern image.

Further, as set forth above, the first embodiment includes just four components of the light sources 444 and 445, the lightguide plate 440, and the image pickup device 443. It is thus advantageous in light of simple construction.

Figure 10:
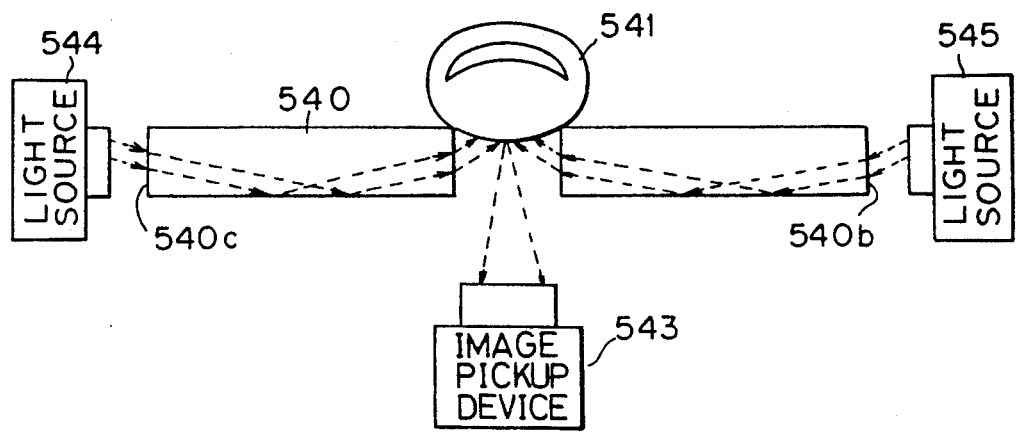
FIG. 10 is a side view schematically showing construction of a fingerprint input apparatus according to a second embodiment of the second invention.
Figure 11:
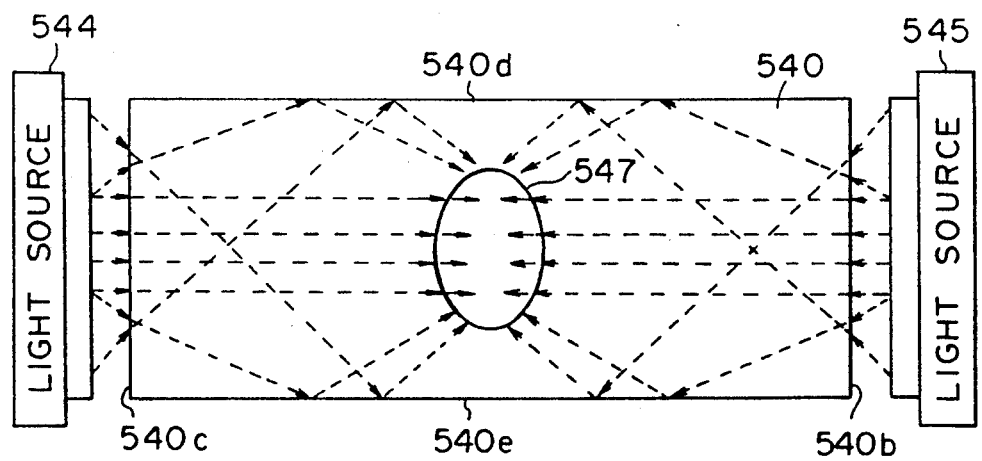
FIG. 11 is a plane view showing the fingerprint input apparatus shown in FIG. 10.

FIG. 10 is a side view schematically showing the construction of a second embodiment of the second invention. FIG. 11 is a plane view showing the second embodiment.

This second embodiment of the second invention is basically likewise to the embodiment shown in FIGS. 8 and 9, except that the two sides 540d and 540e of the lightguide plate 540 are made of mirrors on which metal such as aluminium is vaporized.

The present embodiment makes it possible to propagate the rays of light emitted from right and left light sources 544 and 545 within the lightguide plate 540 as being positively reflected on the two sides 540d and 540e. Finally, the rays of light reach a through hole 547 for picking up a fingerprint. It results in being able to increase the quantity of light reflected on the contour of the fingerprint pattern of the finger 541 and applied to an image pickup device 543, thereby greatly enhancing the S/N ratio.

Figure 12:
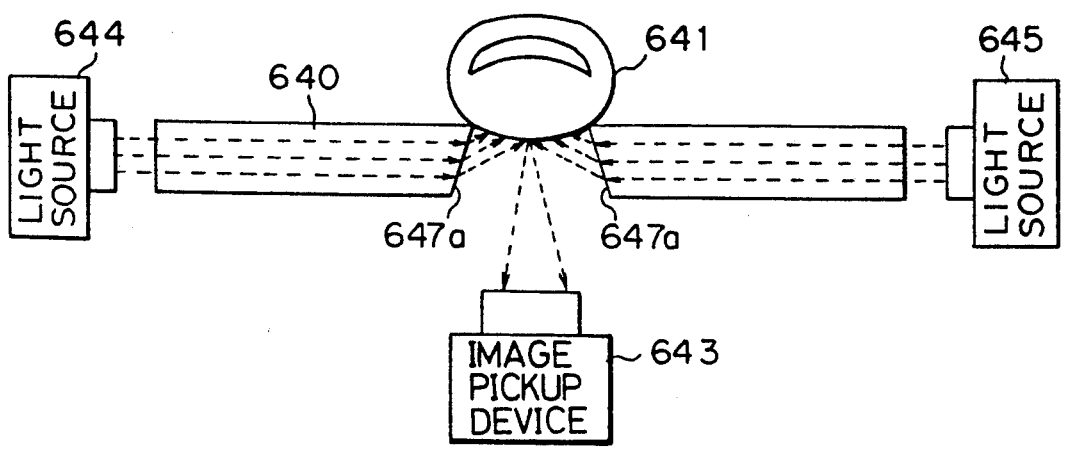
FIG. 12 is a side view schematically showing construction of a fingerprint input apparatus according to a third embodiment of the second invention.
Figure 13:
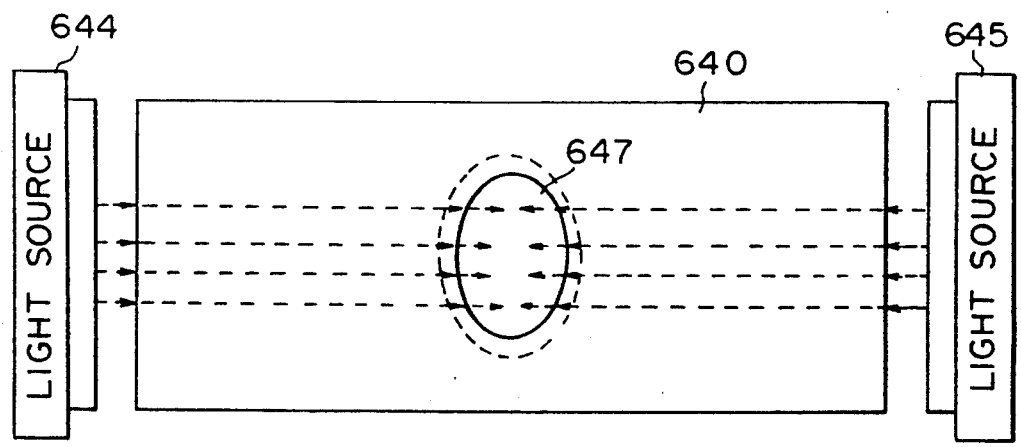
FIG. 13 is a plane view showing the fingerprint input apparatus shown in FIG. 12.

FIG. 12 is a side view showing a third embodiment of the second invention. FIG. 13 is a plane view showing the third embodiment.

The third embodiment of the present invention is basically likewise to the embodiment shown in FIGS. 8 and 9, except that end surfaces 647a of a through hole 647 for picking up a fingerprint are tapered. The embodiment shown in FIGS. 8 and 9 has been designed so that the end surfaces 447a are formed to keep a right angle with the upper and lower surfaces of the lightguide plate 440. On the other hand, the present embodiment is constructed so that the ends 647a are tapered, that is, the through hole 647 spreads downwardly. The rays of light traveled in parallel from light sources 644 and 645 to the through hole 647 through the lightguide plate 640 are greatly refracted on the end surfaces 647a. Hence, a large quantity of light is applied to the fingerprint surface of a finger 641. It results in being able to greatly increase the quantity of light reflected on the contour of the fingerprint pattern of the finger 641 and applied to an image pickup device 643 and greatly enhancing the S/N ratio.

Figure 14:
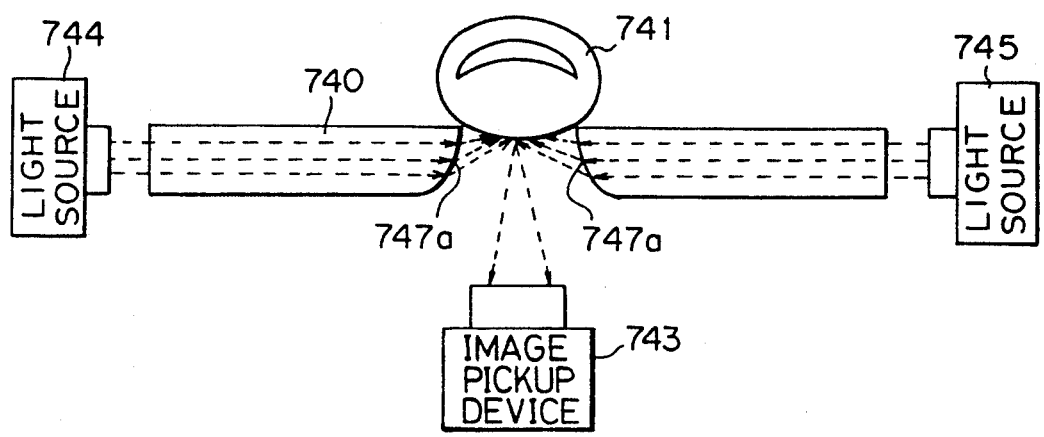
FIG. 14 is a side view schematically showing construction of a fingerprint input apparatus according to a fourth embodiment of the second invention.
Figure 15:
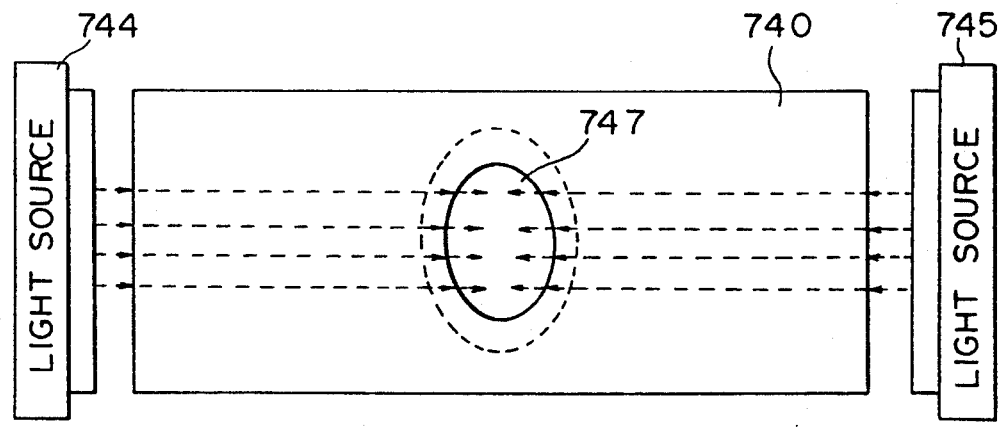
FIG. 15 is a plane view showing the fingerprint input apparatus shown in FIG. 14.

FIG. 14 is a side view schematically showing construction of a fourth embodiment of the second invention. FIG. 15 is a plane view showing the construction of the fourth embodiment.

The third embodiment shown in FIGS. 12 and 13 has been constructed so that the end surfaces 647a of the through hole 647 are linearly tapered. On the other hand, the present embodiment is constructed so that end surfaces 747a of a through hole 747 are progressively spread downwardly in a parabolic manner. The rays of light traveled in parallel from light sources 744 and 745 to the through hole 747 through the lightguide plate 740 are reflected on the end surfaces 747a in a manner to be focused on the fingerprint surface of a finger 741. It results in being able to greatly increase the quantity of light reflected on the contour of the fingerprint pattern of the finger 741 and applied to an image pickup device 743 and to greatly enhance the S/N ratio.

As set forth above, the second invention including the foregoing first to fourth embodiments basically includes the light sources, the lightguide plate having a hole formed thereon, and the image pickup device. Hence, it enables to provide a very small and inexpensive fingerprint input apparatus. Further, since the fingerprint surface is not in contact with the lightguide plate, it is possible to keep the surface of the lightguide plate cleaner than the apparatus requiring a finger to be in contact with the lightguide plate. Hence, the second invention is capable of overcoming the adverse effect of the dirt increased as more persons contact their fingers on the lightguide plate. According to the fingerprint input apparatus constructed to contact a finger on the lightguide plate or the prism, the dirt is progressively increased on the lightguide plate and the prism. The increased dirt may give an adverse effect to the S/N ratio, resulting in becoming disable to identify or collate the fingerprint. Further, in case the previous fingerprint pattern is often left on the lightguide plate or the prism, there is a possibility that a fingerprint is erroneously identified or collated.

Moreover, the second invention makes it possible to positively secure the finger with the through hole and hit a ray of light to the fingerprint surface at a low angle of incidence, thereby allowing the fingerprint pattern to be more clearly emerged. It results in being able to greatly enhance the S/N ratio.

Next, the description will be directed to a first embodiment of the third invention.

Figure 16:
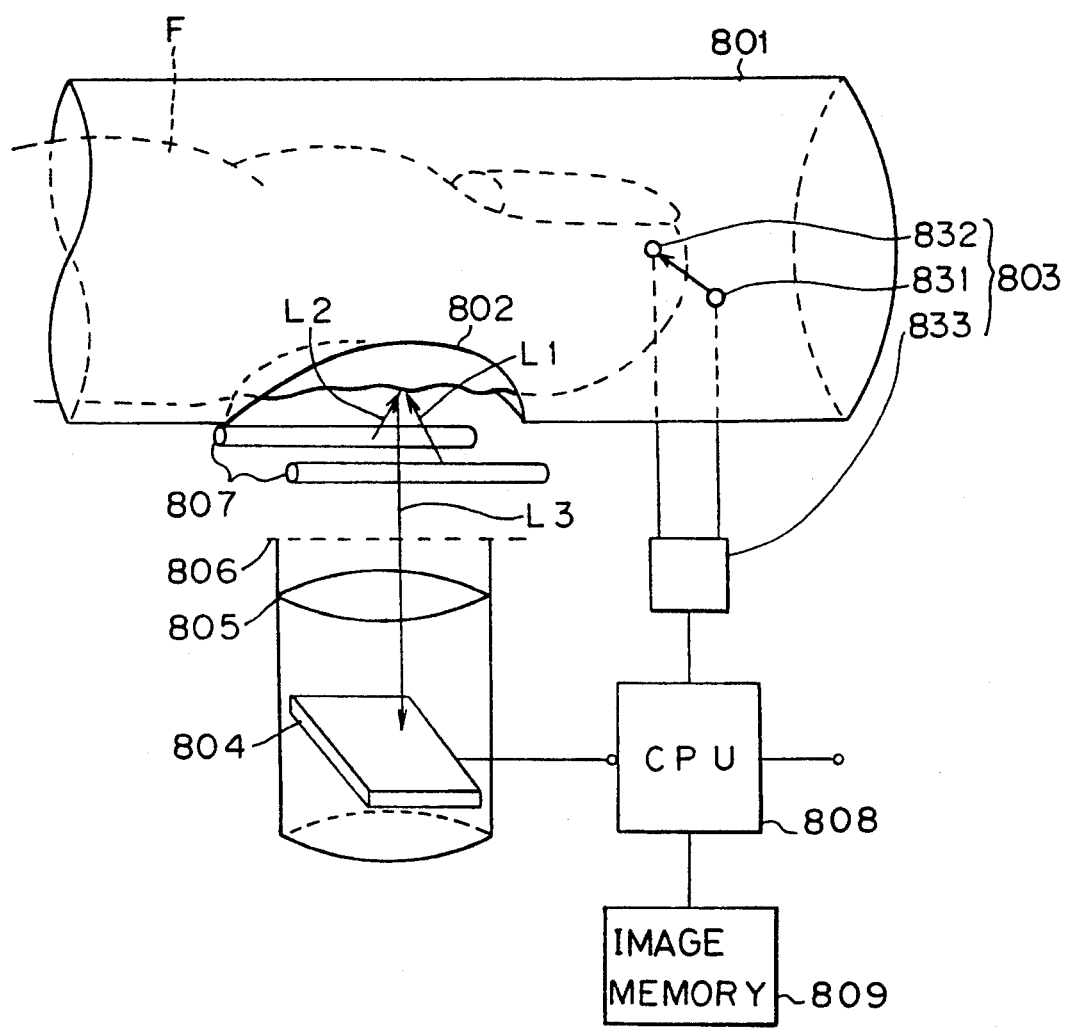
FIG. 16 is a diagram showing a fingerprint input apparatus according to a first embodiment of the third invention.

FIG. 16 is a diagram showing the fingerprint input apparatus according to the first embodiment of the third invention. As shown, the fingerprint input apparatus includes a cylindrical finger guide 801 for guiding a tip of a finger F to be inserted for picking up the fingerprint, an opening window 802 formed on the finger guide 801, an image pickup starting switch 803 to be operated when the finger tip inserted in the finger guide 801 is sensed, a two-dimensional image sensor (Charge-Coupled Device, for example) 804 for picking up a fingerprint image in response to an image pickup start signal given when the image pickup starting switch 803 has sensed the finger tip, a lens 805, a dust cover 806 for protecting a lens system from dust, a lighting device 807 for lighting an assumed fingerprint surface through the opening window 802, and a CPU 808 for controlling the output of the image pickup start signal to the lighting device 807 and the image sensor 804 and the write of the picked up fingerprint image into an image memory 809 based on the input signal sent from the image pickup starting switch 803.

The CPU 808 includes a signal line leading to an external interface in addition to the image memory 809. The image pickup starting switch 803 is composed of a light source 831, a light detector 832 and a switch 833. The image pick up starting switch 803 is operated off when the light detector 832 detects light and on when it detects no light. The lighting device 807 employs two linear light sources such as a fluorescent tube so that a belly of the finger tip is lit from both sides by these two light sources for unifying a tone of the fingerprint image. The lens 805 and the image sensor 804 define a resolution of 10 pixels/mm to 20 pixels/mm. The focal distance of the lens 805 should be 2 mm or longer for clearly capturing the fingerprint image, because the height difference of the fingerprint surface is 2 mm at maximum.

Next, the description will be directed to how the fingerprint input apparatus operates.

At first, someone inserts his or her finger F along the cylindrical finger guide 801. When the tip of the finger F is inserted into a predetermined depth, that is, the fingerprint surface is entered into the area where the two-dimensional image sensor 804 enables to pick up the fingerprint image through the opening window 802, the image pickup starting switch 803 is turned on when the light is cut and feeds a signal for sensing the finger tip to the CPU 808. In response to the signal, the CPU 808 serves to output a lighting signal to the lighting device 807. Then, the rays of light L1 and L2 emitted from the lighting device 807 pass through the opening window 802 to the fingerprint surface on which the rays of light L1 and L2 are reflected. The reflected light L3 is sent to the two-dimensional image sensor 804 through the lens 805. The two-dimensional image sensor 804 serves to form a density image representing ridges and valleys of the fingerprint. At a time, the CPU 808 serves to send out the image pickup start signal to the two-dimensional image sensor 804 so that the two-dimensional image sensor 804 writes the fingerprint image on the image memory 809.

The inventors of the present invention know that the fingerprint input apparatus is constructed to pick up the fingerprint image with the fingerprint surface being in contact with a glass surface. Hence, it has an image sensor whose light-receptacle surface is directed upwardly, because a subject person can easily recognize a finger-contacting surface and it is easy to do maintenance of the apparatus. Since the light-receptacle surface is directed upward, the adverse effect of noises may degrade the fingerprint image. The foregoing first embodiment of this invention provides the dust cover 806 for protecting the lens system from dust dropped from the opening window 802.

For obtaining a more efficient dust-preventing effect, the fingerprint input apparatus according to the first embodiment provides the finger guide which allows the upward-directed fingerprint surface to be directed in the range between the 90° right and the 90° left and the lower-directed lens surface to be directed in the range between the 90° right and the 90° left.

Figure 17:
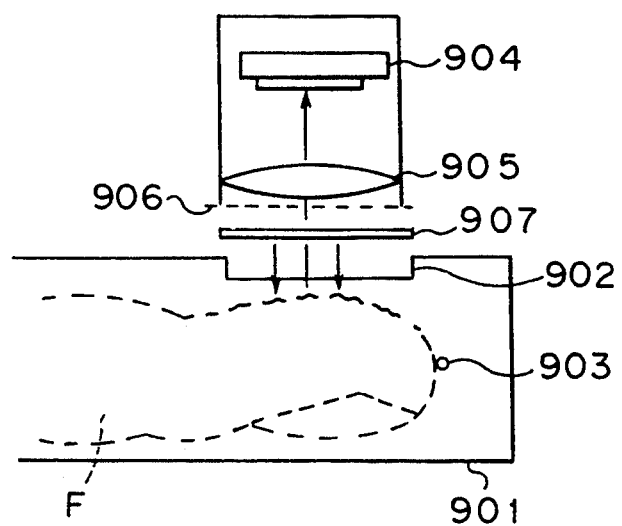
FIG. 17 is a diagram showing a fingerprint input apparatus according to a second embodiment of the third invention.

FIG. 17 is a diagram showing a second embodiment of the third invention which allows a fingerprint surface to be upward directed when a finger F is inserted. As shown, the present fingerprint input apparatus includes a finger guide 901, an opening window 902, an image pickup starting switch 903, a two-dimensional image sensor 904, a lens 905, a dust cover 906, and a lighting device 907. Those components operate in a similar manner to those of the foregoing first embodiment of this invention. As viewed in FIG. 17, the two-dimensional image sensor 904 provides a light-receptacle surface directed downwardly so as to protect the surface from dust.

Figure 18:
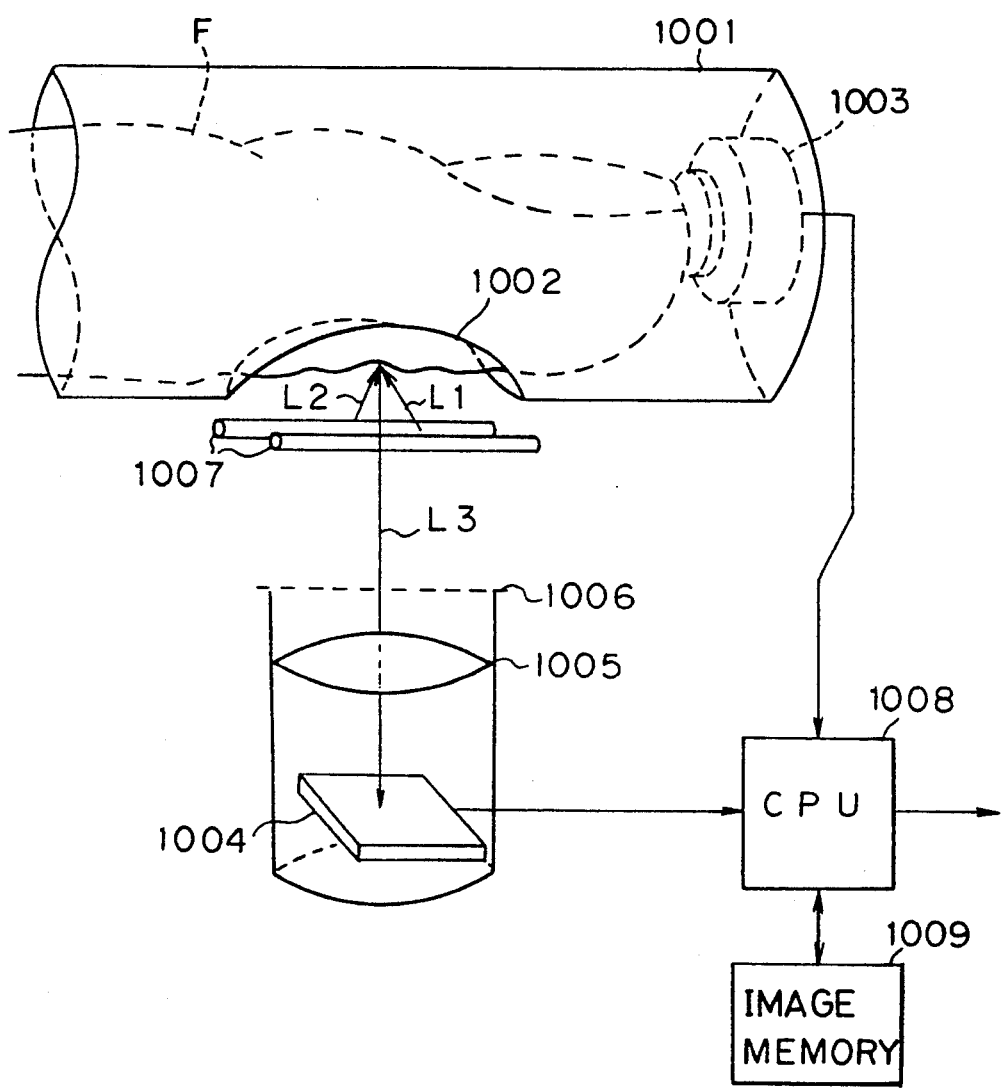
FIG. 18 is a diagram showing a fingerprint input apparatus according to a third embodiment of the third invention.

FIG. 18 is a diagram showing a third embodiment of the third invention. As shown the fingerprint input apparatus according to the third embodiment includes a finger guide 1001, an opening window 1002, a push-type switch 1003 for sensing the tip of a finger F inserted into the finger guide 1001, a two-dimensional image sensor 1004, a lens 1005, a dust cover 1006, a lighting device 1007, a CPU 1008, and an image memory 1009. Those components except the push-type switch 1003 operate in a similar manner to those of the first embodiment of the third invention. Hence, the description about those components is omitted.

The push-type switch 1003 is a mechanical image pickup starting switch. The push-type switch 1003 is operated on when the finger tip pushes the push-type switch 1003, and sends a signal for starting an image to the CPU 1008. With this mechanical switch, the finger is fixed when it is imaged so that the fingerprint image is picked up with little positional slippage.

Figure 19:
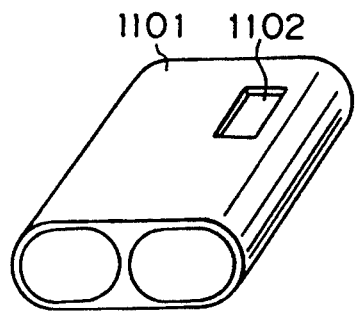
FIG. 19 is a perspective view showing an outer appearance of a finger guide included in the fingerprint input apparatus.

FIG. 19 is a perspective view showing an outer appearance of another finger guide. A finger guide 1101 provides two cylindrical guides which allow two fingers to be inserted at the same time. It results in being able to prevent the finger tip from being slipped in the turning direction, because it is found that the insertion of two or more fingers into the cylindrical guides stops the turning slippage of a finger from a human engineering point of view. Reference numeral 1102 denotes an opening window on a normal line along which the two-dimensional image sensor is located. If three cylindrical guides are arranged, they make it possible to more effectively prevent the finger tip from being slipped. Further, these three cylindrical guides respectively provide opening windows on normal lines along which the corresponding number of two-dimensional image sensors are located for picking up two or more fingerprint images and concurrently collating them. It results in lowering ambiguity appearing in the fingerprint recognition and improving the reliability.

Next, the description will be directed to the fourth invention. At first, a first embodiment of the fourth invention will be described.

Figure 20:
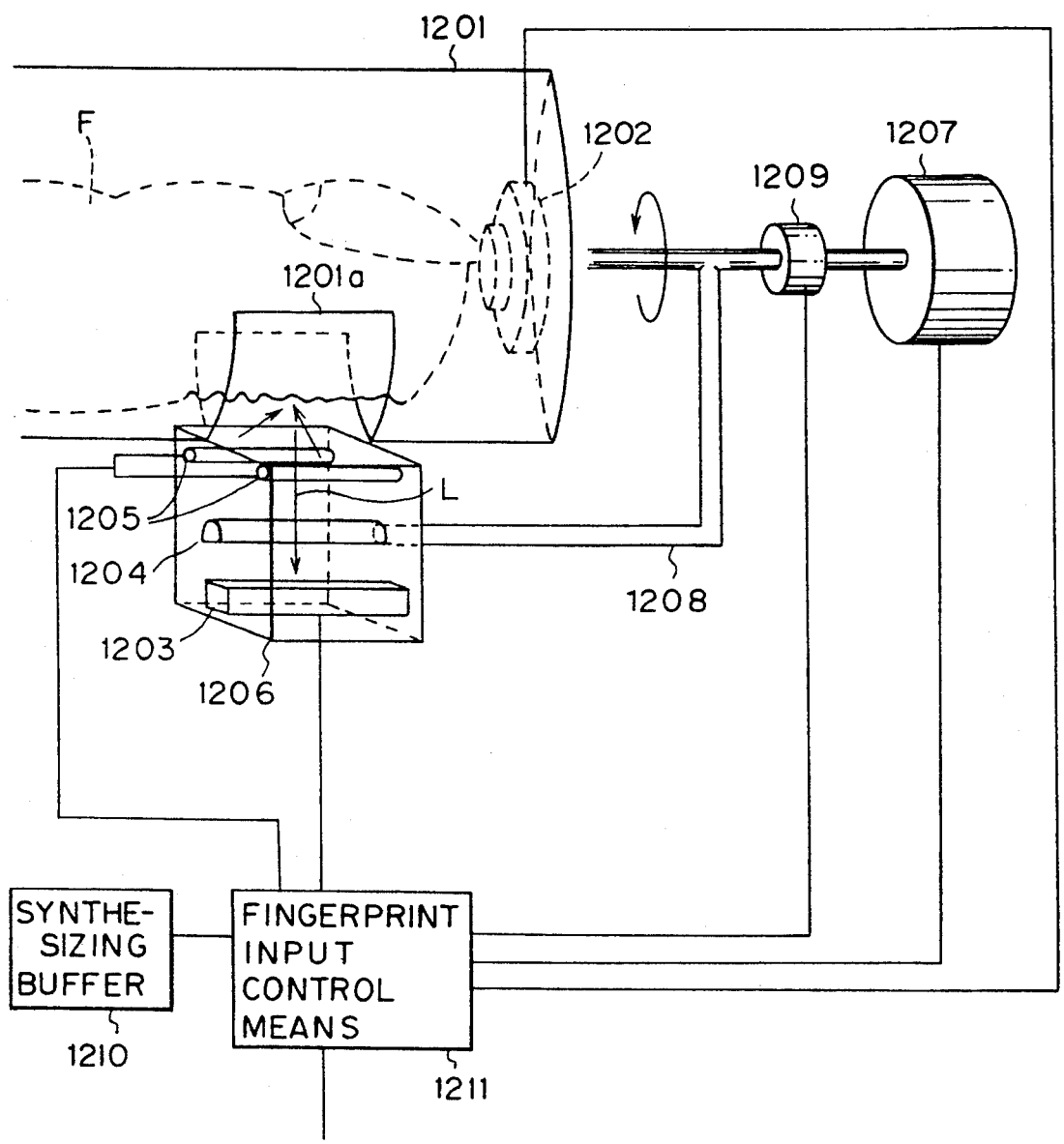
FIG. 20 is a diagram showing a fingerprint input apparatus according to a first embodiment of the fourth invention.

FIG. 20 is a diagram showing a fingerprint input apparatus according to the first embodiment of the fourth invention. As shown, the fingerprint input apparatus includes a cylindrical finger guide 1201 for guiding a finger tip to be inserted therein, an opening window 1201a provided in correspondence with an assumed place on which a fingerprint surface is put, an image pickup starting switch 1202 located at the bottom of the finger guide 1201 so as to be operated by the inserted finger tip, a one-dimensional image sensor 1203 (referred to as an image sensor) for picking up part of a fingerprint image in response to a image pickup start signal given when the image pickup starting switch 1202 has sensed the finger tip, a cylindrical lens 1204, a lighting device 1205 having a pair of lighting sources arranged parallel to the image sensor 1203 and serving to light the assumed place of the fingerprint surface through the opening window 1201a, a supporting base 1206 for supporting the image sensor 1203, the lens 1204, and the lighting device 1205 integrally, a driving unit 1207 and a crank shaft 1208 serving to rotate the supporting base 1206 on the central axis of the cylindrical finger guide 1201 along the opening window 1201a, an angle sensor 9 for sensing an angle of rotation of the driving unit 7, and a CPU 1211 for executing some controls in response to the input signal sent from the image pickup starting switch 1202.

The CPU 1211 serves to supply an imaging-start signal to the image sensor 1203, the lighting device 1205, and the driving unit 1207 in response to the input signal sent from the image pickup starting switch 1202, sequentially transfer the picked up one-dimensional image to a synthesizing buffer 1210 in response to the output signal sent from the angle sensor 1209, and instruct the synthesizing buffer 1210 to supply the two-dimensional fingerprint image. The CPU 1211 includes a signal line leading to an external interface in addition to the synthesizing buffer 1210.

The lighting device 1205 employs a pair of linear light sources such as fluorescent tubes so that a belly of the finger tip are lit from both sides of the image sensor 1203 by these two light sources for unifying a tone of the fingerprint image. The lens 1204 and the image sensor 1203 defines a resolution of 20 pixels/mm to 30 pixels/mm. The focal distance of the lens 1204 should be 2 mm or longer for clearly capturing the fingerprint image, because the height difference of the fingerprint surface is 2 mm at maximum.

Next, the description will be directed to how the fingerprint input apparatus operates.

At first, someone inserts his or her finger F along the cylindrical finger guide 1201. When the tip of the finger F is inserted into a predetermined depth, that is, the fingerprint surface is entered into the area where the one-dimensional image sensor enables to pick up the fingerprint image through the opening window 1201a, the image pickup starting switch 1202 is turned on with the finger tip being pressed. The image pickup starting switch 1202 sends a finger-sensing (to-be-imaged) signal to the CPU 1211. In response to the signal, the CPU 1211 outputs the lighting signal to the lighting device 1205 and initializes the synthesizing buffer 1210. Then, the rays of light emitted from the lighting device 1205 are reflected on the fingerprint surface through the opening window 1201a. The reflected light L is entered into the image sensor 1203 through the lens 1204. The image sensor 1203 serves to form a one-dimensional density image representing ridges and valleys formed on the fingerprint surface. At a time, the CPU 1211 sends a drive-start signal to the driving unit 1207 and an image pickup start signal to the image sensor 1203, then one-dimensional image data $g(\theta i)$ is transferred to the synthesizing buffer 1210. $\theta i$ denotes an angle of rotation sensed by the angle sensor 1209. Every time the sensed rotation angle $\theta i$ reaches a positive number multiple of a rotation angle r corresponding to a pixel pitch, the CPU 1211 outputs an imaging signal to the image sensor 1203. Every time the driving unit 1207 rotates by the rotation angle r, the one-dimensional image $g(\theta i)$ is transferred to the synthesizing buffer 1210 wherein the one-dimensional image $g(\theta i)$ is synthesized for composing a two-dimensional image.

FIG. 21A is a view showing relation between the finger tip and the rotation of the image sensor 1203 interlocked with the rotation of the driving unit 1207. FIG. 21B is a model view showing the two-dimensional fingerprint image composed by synthesizing the one-dimensional image $g(\theta i)$ transferred from the image sensor 1203 every time the driving unit 1207 is rotated by the rotation angle r. The rotation angle r should be arranged so that the pixel pitch is 50 μm or less.

When the driving unit 1207 rotates by a predetermined rotation angle $\theta e$, the CPU 1211 sends out a signal indicating reverse rotation to the driving unit 1207 for reverting the image sensor 1203 to the initial rotation angle $\theta s$. This is the end of the imaging operation, when the inputting operation of the fingerprint image is terminated.

Figure 22:
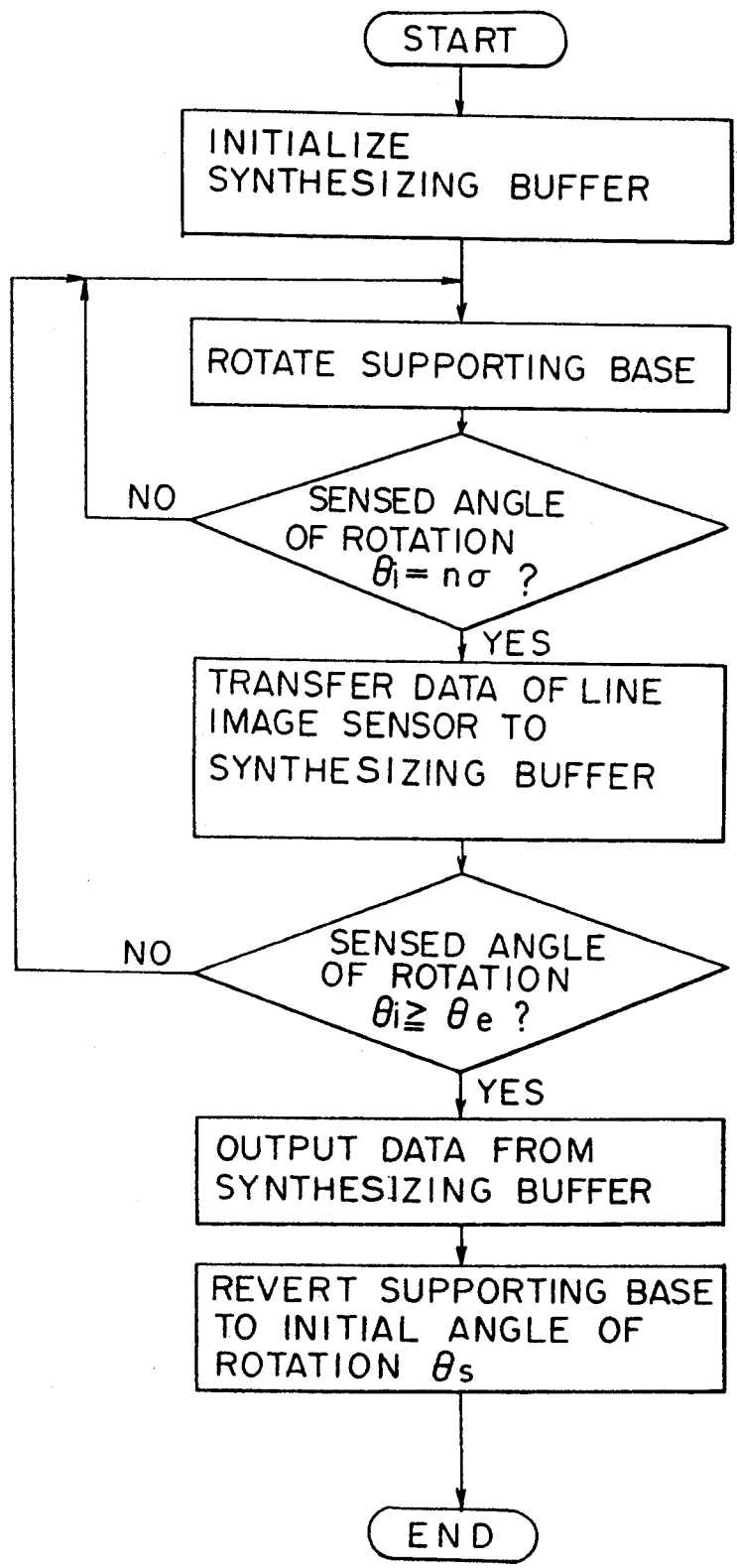
FIG. 22 is a flowchart showing the process executed in the fourth invention.

FIG. 22 is a flowchart showing the imaging operation mentioned above. According to the foregoing embodiment, at first, the synthesizing buffer 1210 is initialized. Then, as the one-dimensional image sensor 1203 and the lighting device 1205 are rotated in concert, the one-dimensional image formed with uniform illuminance is sequentially picked up by the synthesizing buffer 1210 where those images are synthesized for composing a two-dimensional fingerprint image with uniform luminance.

Further, it is possible to input the fingerprint image at regular pitches on the overall surface (both sides) of the fingerprint surface of the finger. This feature, thus, makes it possible to guarantee the collation or identification of a partially abraded fingerprint.

Figure 23:
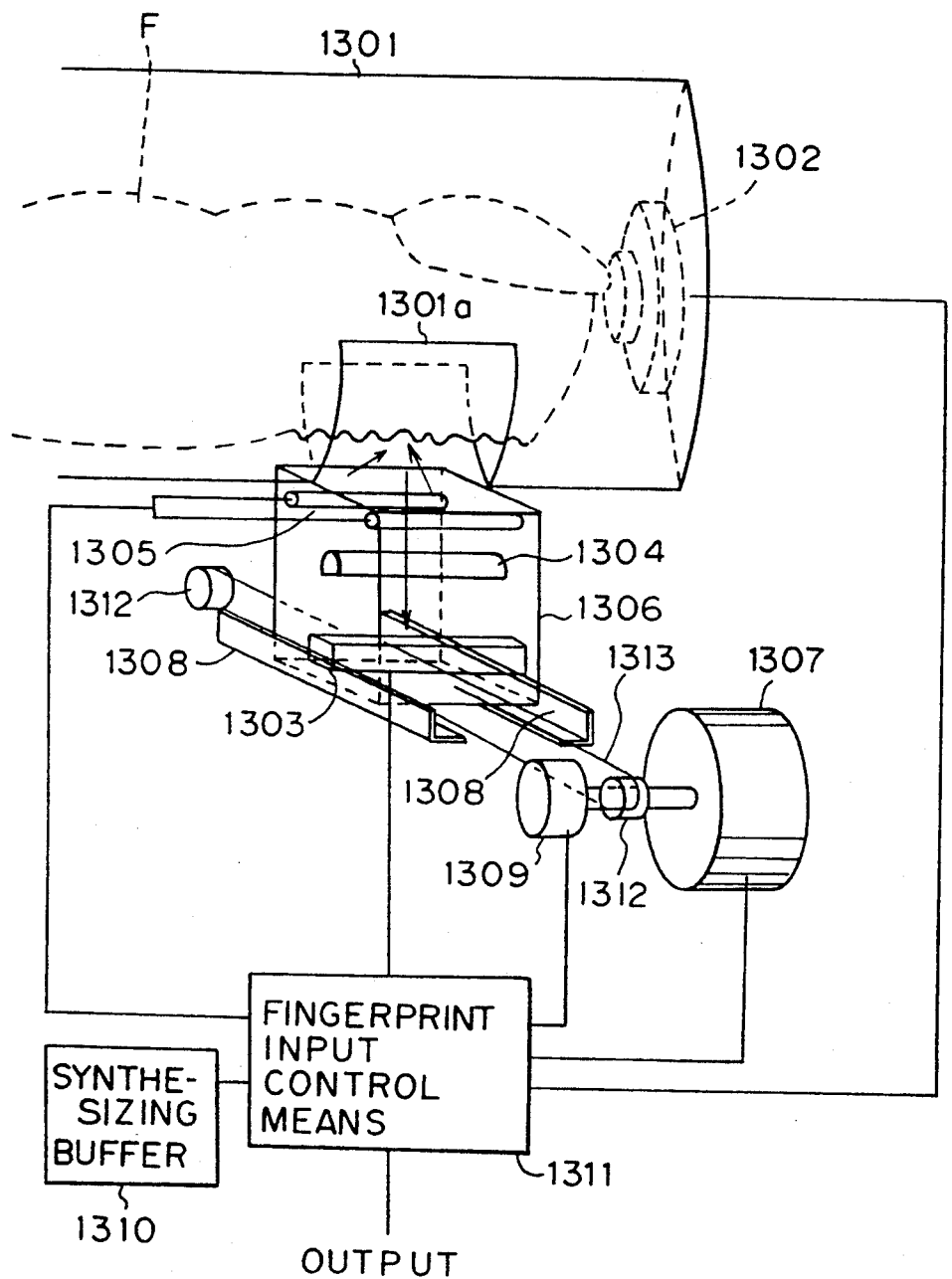
FIG. 23 is a diagram showing a fingerprint input apparatus according to a second embodiment of the fourth invention.

FIG. 23 is a diagram showing a fingerprint input apparatus according to the second embodiment of the fourth invention. This fingerprint input apparatus is constructed to horizontally move an image sensor, a lens, and a lighting device in concert. As shown, the fingerprint input apparatus includes a finger guide 1301, an opening window 1301a, an image pickup starting switch 1302, a one-dimensional line image sensor 1303, a lens 1304, a lighting device 1305, a supporting base 1306, a driving unit 1307, a guide rail 1308, an angle sensor 1309, a synthesizing buffer 1310, a CPU 1311, a pulley 1312, and a belt 1313. This fingerprint input apparatus operates on the substantially similar principle to the apparatus according to the first embodiment of the fourth invention shown in FIG. 20. Hence, this embodiment will be briefly described with reference to FIG. 23.

When a finger F is inserted into the finger guide 1301, the image pickup starting switch 1302 is turned on with a finger tip being pushed thereon. When the lighting device 1305 is lit, the synthesizing buffer 1310 is initialized. At a time, the CPU 1311 sends out a drive-start signal to the driving unit 1307 and an imaging signal to the image sensor 1303 from which the one-dimensional image is transferred to the synthesizing buffer 1310. When the driving unit 1307 is rotated, the pulley 1312 serves to move the belt 1313. The movement of the belt 1313 causes the supporting base 1306 to be horizontally moved along the guide rail 1308. With the movement of the supporting base 1306, the image sensor 1303, the lens 1304, and the lighting device 1305 are horizontally moved in concert. Every time the angle of rotation sensed by the angle sensor 1309 reaches a positive number multiple of the rotation angle corresponding to the pixel pitch, the CPU 1311 sends out the imaging signal to the image sensor 1303 for instructing the image sensor 1303 to transfer the one-dimensional image captured along the horizontal movement of the image sensor 1303 to the synthesizing buffer 1310 where the two-dimensional image is composed.

When the driving unit 1307 is rotated by a predetermined rotation angle, the CPU 1311 sends out a signal indicating reverse rotation to the driving unit 1307 for the purpose of reverting the image sensor 1303 to the initial rotation angle. This is an end of the imaging operation, when the inputting operation of the fingerprint image is terminated. According to the foregoing second embodiment of the fourth invention, the fingerprint input apparatus makes it possible to sequentially pick up a one-dimensional image with uniform luminance by moving the image sensor and the lighting device in concert and obtain a two-dimensional fingerprint image with uniform luminance by synthesizing the sequentially picked-up one-dimensional images. In this embodiment, the supporting base 1306 may be moved to and fro.

It goes without saying that the fourth invention is not limited to the foregoing embodiments. The invention may employ the finger guide constructed so that the fingerprint surface is directed upwardly in the range of the right 90° to the left 90° and the lens and the image sensor constructed so that the lens surface and the light-receptacle surface of the image sensor are directed downwardly in the range of the right 90° to the left 90°. According to the invention so constructed, the downwardly-directed optical system is little influenced by the dust, which otherwise would have dropped to the optical system.

As another construction, it may be possible to provide two cylindrical guides in the finger guide for receiving two fingers at a time. The insertion of the two fingers allows the finger tip to be secured at a right position without slipping. It is found that the insertion of two or more fingers into the cylindrical guides stops the rotation from a human engineering point of view. In this instance, the cylindrical guides provides the corresponding opening windows so that one image sensor enables to pick up two or more fingerprint images and collate them in a concurrent manner, resulting in lowering ambiguity of the fingerprint identification or collation and enhancing the reliability.

In addition, the user may feel relived in case the apparatus has a capability of reporting the fingerprint-inputting process to the user.

In turn, the description will be directed to the fifth invention. Like the first to the fourth invention, the fifth invention can take some embodiments. At first, a first embodiment of the fifth invention will be described with reference to FIGS. 24 and 25.

Figure 24:
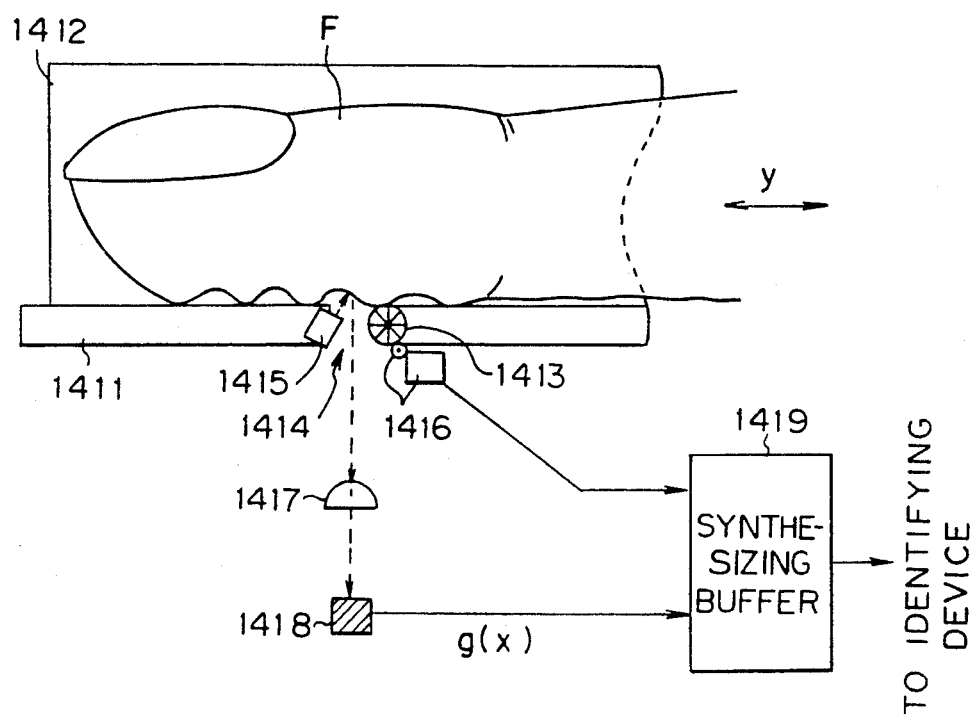
FIG. 24 is a schematic diagram showing a fingerprint input apparatus according to a first embodiment of a fifth invention.
Figure 25:
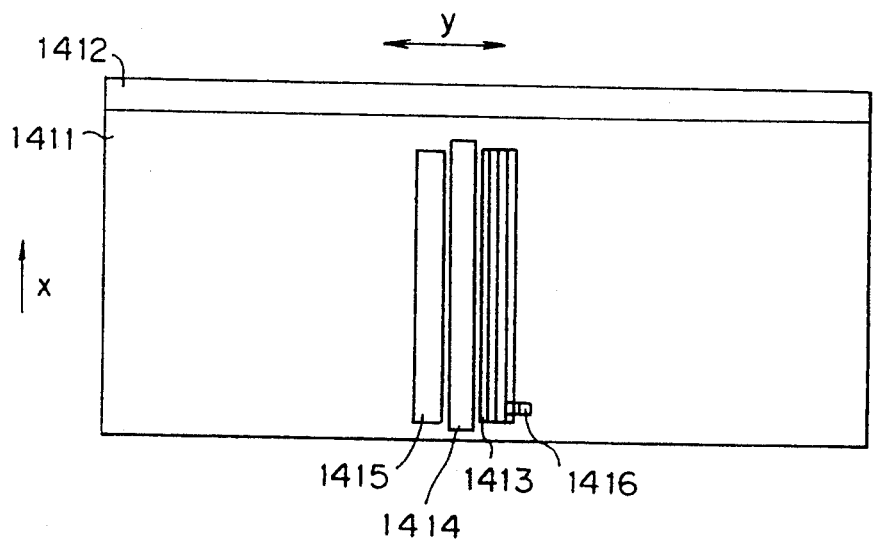
FIG. 25 is a plane view showing an essential portion of the fingerprint input apparatus shown in FIG. 24.

FIG. 24 is a schematic diagram showing a fingerprint input apparatus according to the first embodiment of the fifth invention. FIG. 25 is a plane view showing an essential portion of the fingerprint input apparatus shown in FIG. 24.

With reference to FIGS. 24 and 25, the fingerprint input apparatus includes a fingerprint input base 1411, a guide plate 1412, a roller 1413, a slit 1414, a lighting device 1415, a rotary encoder 1416, a cylindrical lens 1417, a line image sensor 1418, and a synthesizing buffer 1419.

The fingerprint input base 1411 is made tabular so that the fingerprint surface of a finger F is allowed to longitudinally move. It is located in a horizontal manner as viewed in FIG. 24.

The guide plate 1412 is formed on the sides of the fingerprint input base 1411 so as to prevent the finger F from being slipped in the wide direction (in the x-direction viewed in FIG. 25).

The roller 1413, the slit 1414, and the lighting device 1415 are all located on the fingerprint input base 1411.

The finger F is moved in the y-direction viewed in FIGS. 24 and 25 in contact with the fingerprint input base 1411 and the roller 1413, thereby allowing the roller 1413 to rotate. The lighting device 1415 is located so that the ray of light is emitted from the lighting device 1415 to the fingerprint surface placed on the slit 1414 and is reflected right downwardly from the fingerprint surface.

The roller 1413, the slit 1414, and the lighting device 1415 are disposed in the lateral direction of the finger F, that is, the x-axis direction perpendicular to the y-axis direction, that is, the moving direction of the finger F.

The rotary encoder 1416 is located under the fingerprint input base 1411 and the roller 1413 and is connected to the synthesizing buffer 1419. The rotary encoder 1416 is located so that it enables to sense the amount of rotation of the roller 1413.

The cylindrical lens 1417 is located right below the slit 1414 of the fingerprint input base 1411 so that the light reflected on the fingerprint surface of the finger F is allowed to be parallelized. Further, the cylindrical lens 1417 employs a deep focal depth which shortens an optical length and thereby reduces the overall apparatus in size.

The line image sensor 1418 is located lower than the cylindrical lens 1417 located right under the slit 1414 of the fingerprint input base 1411 and is connected to the synthesizing buffer 1419. The line image sensor 1418 is located so that it enables to read the light reflected on the fingerprint surface, which reflected light is parallelized by the cylindrical lens 1417 before being read.

The rotary encoder 1416 provides a minimum sensing amount s of about 50 µm per one pixel. The line image sensor 1418 also provides a reading accuracy r of about 50 µm per one pixel.

The synthesizing buffer 1419 is connected to an identifying device (not shown) for identifying the input fingerprint pattern.

Figure 26:
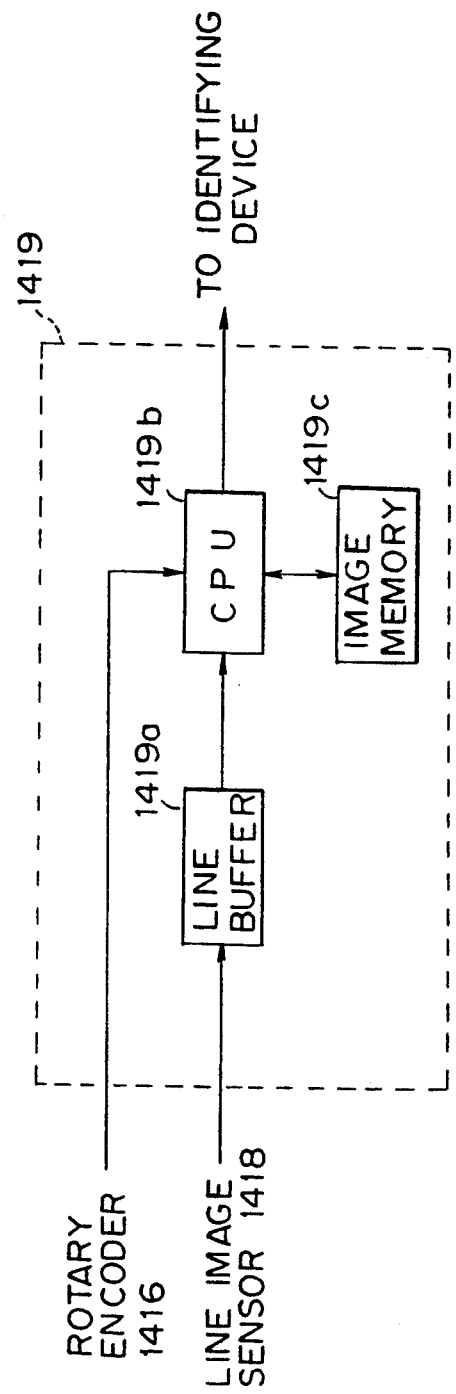
FIG. 26 is a block diagram showing a synthesizing buffer included in the fingerprint input apparatus shown in FIG. 24.
Figure 27:
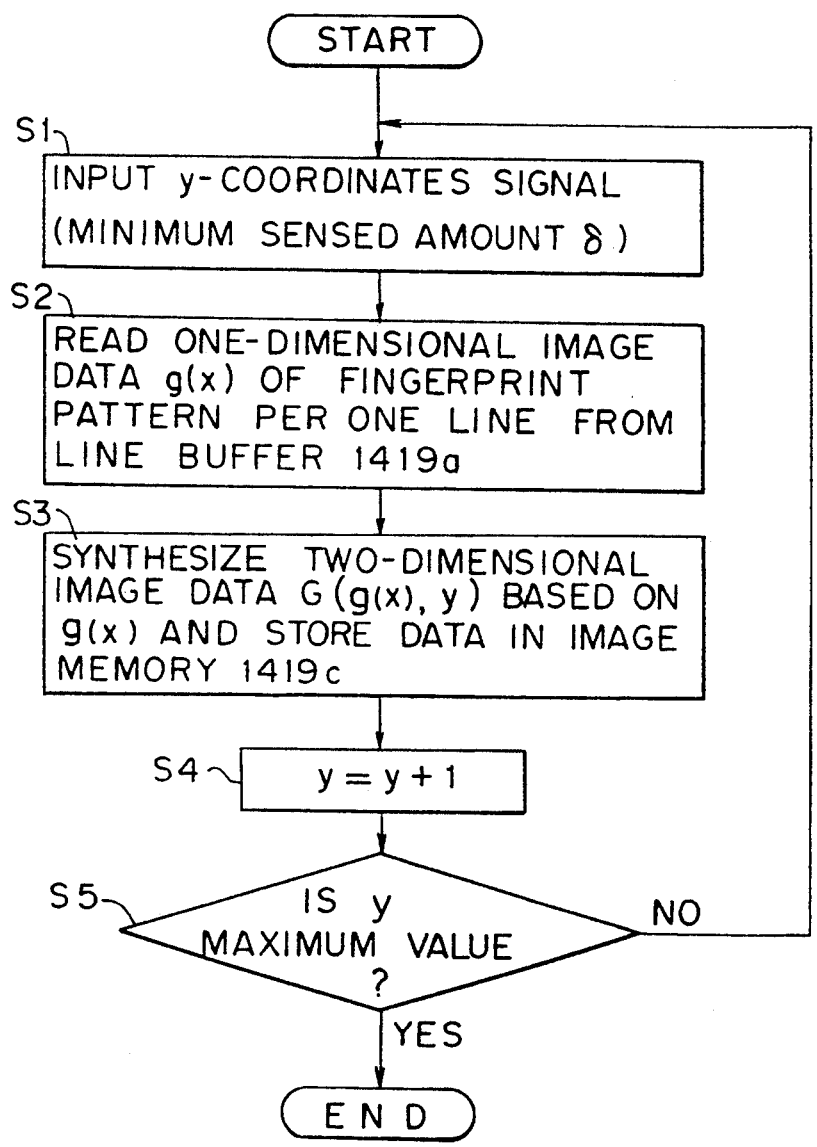
FIG. 27 is a flowchart showing the process of the fingerprint input apparatus shown in FIG. 24.

FIG. 26 is a block diagram showing arrangement of the synthesizing buffer 1419 shown in FIG. 24. FIG. 27 is a flowchart for illustrating the operation of the fingerprint input apparatus shown in FIG. 24.

As shown in FIG. 26, the synthesizing buffer 1419 includes a line buffer 1419a, a CPU 1419b, and an image memory 1419c.

The line buffer 1419a is constructed so that it enables to store a one-dimensional image data g(x) per one line which are read and converted into a digital value by the line image sensor 1418.

The CPU 1419b operates in accordance with the flowchart shown in FIG. 27, which will be described in detail later.

The image memory 1419c is capable of storing the two-dimensional image data representing the fingerprint pattern of the finger F.

Figure 28:
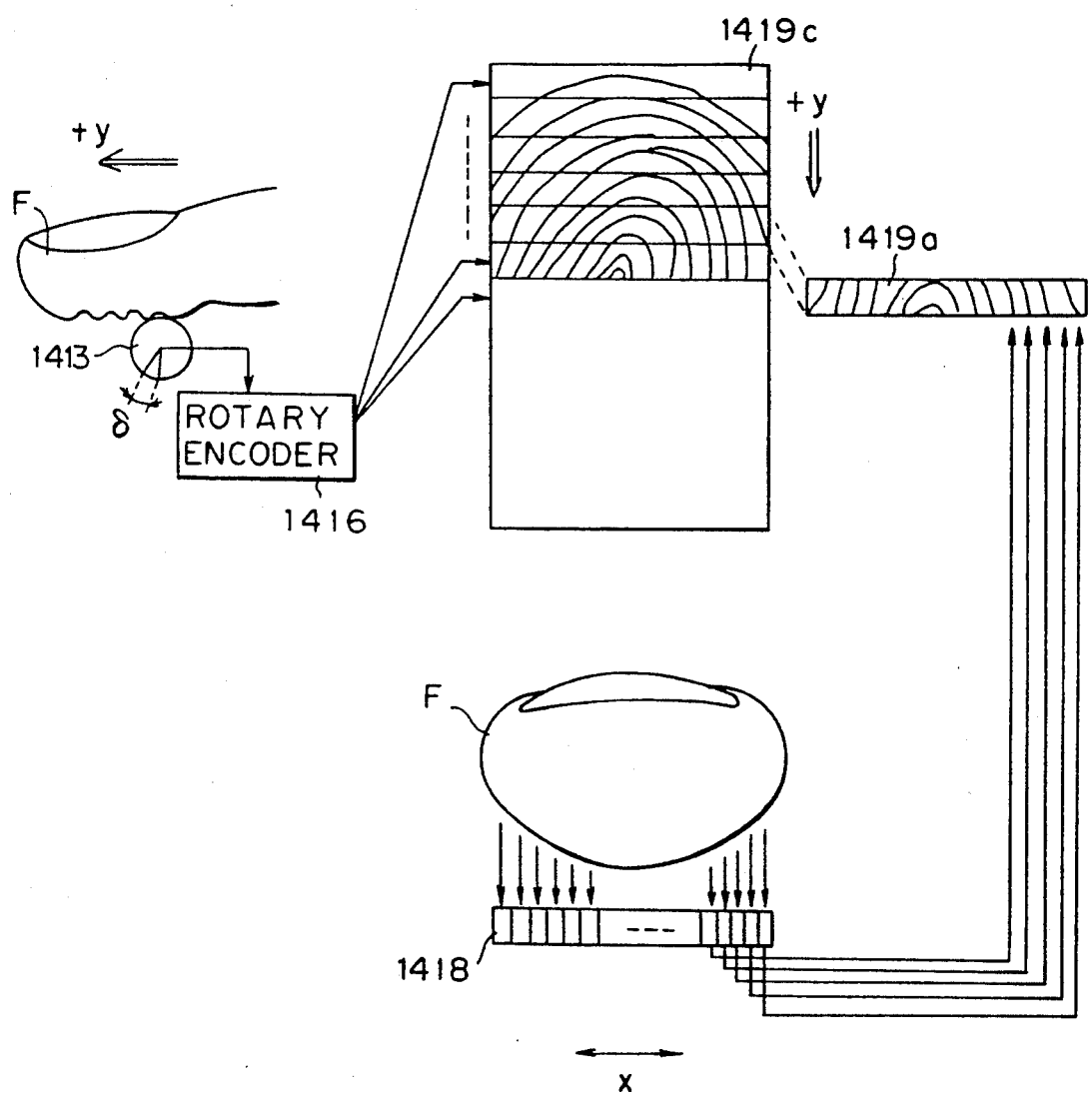
FIGS. 28 and 29 are views for describing the operation of the fingerprint input apparatus shown in FIG. 24.
Figure 29:
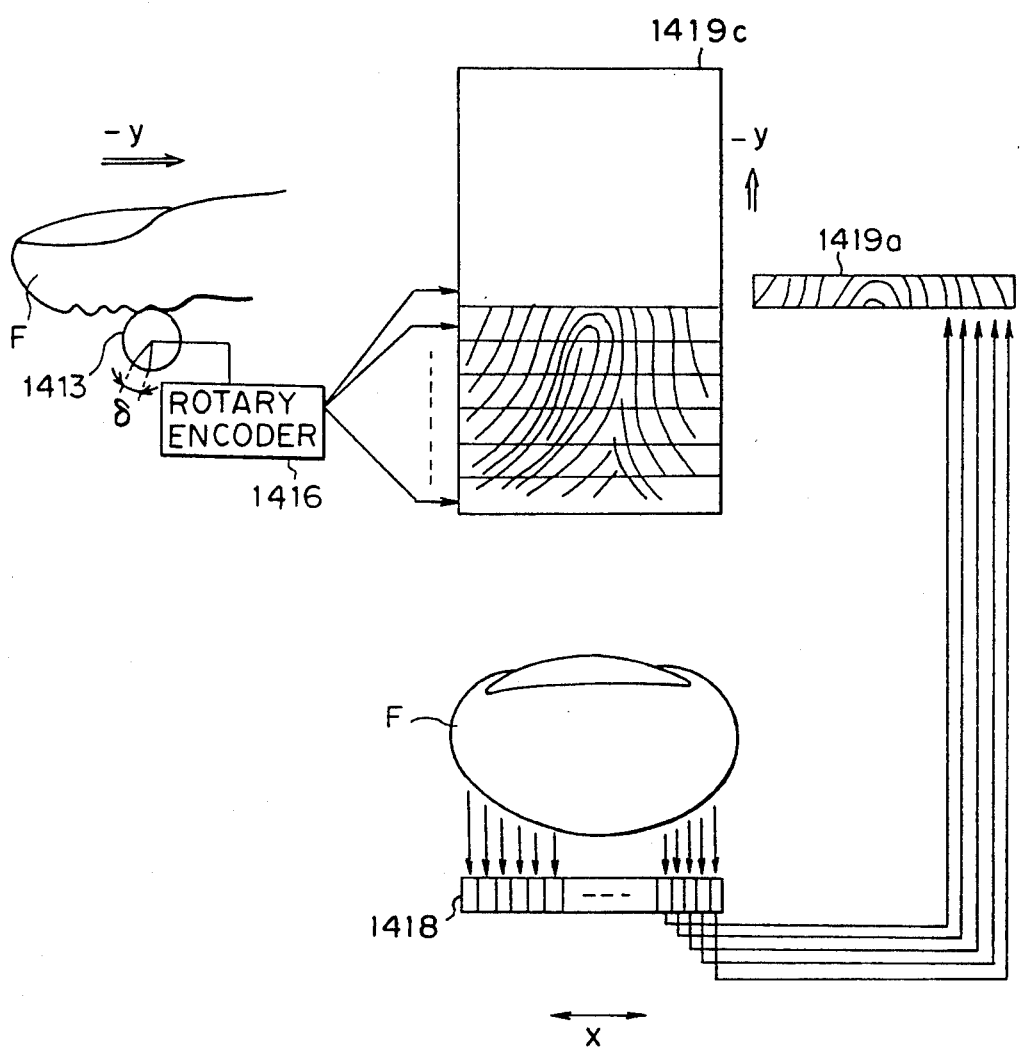

FIGS. 28 and 29 are views for describing the operation of the fingerprint input apparatus shown in FIG. 24.

With reference to FIGS. 27 to 29, the operation of the first embodiment of the fifth invention, in particular, of the CPU 1419b will be described in detail.

When the finger F is moved in the y-axis direction (as viewed in FIGS. 24 and 25) in contact with the fingerprint input base 1411 and the roller 1413, the roller 1413 is allowed to rotate.

The rotation amount of the roller 1413 is sensed by the rotary encoder 1416. The rotary encoder 1416 serves to generate a pulse and a rotating direction signal (sign) for each minimum sensing amount r and output these signals to the synthesizing buffer 1419.

The line image sensor 1418 reads the light reflected on the fingerprint surface of the finger F, which has been parallelized by the cylindrical lens 1417 before being read. Then, the line image sensor 1418 serially outputs the read signal to the synthesizing buffer 1419.

As shown in FIG. 28, consider that the finger F is moved from the roller 1413 to the lighting device 1415 (in the +y-axis direction) in a manner that the finger is in contact with the roller 1413, that is, the finger F is moved on the slit 1414 in the direction of a first joint to a second joint of the finger F. The rotary encoder 1416 outputs to the CPU 1419b a y-coordinate signal consisting of a pulse for each minimum sensing amount s and a positive (+y) rotating direction signal.

The fingerprint surface of the finger F is lit up by the lighting device 1415. The light reflected on the fingerprint surface passes through the slit 1414 and is shaped into parallel rays of light through the cylindrical lens 1417. The resulting rays of light are read by the line image sensor 1418. Then, the line buffer 1419a sequentially stores those rays of light as the one-dimensional image data g(x) per one line.

As shown in FIG. 27, when the CPU 1419b receives the y-coordinate signal from the rotary encoder 1416 (step S1), the CPU 1419b reads out the one-dimensional image data g(x) per one line stored in the line buffer 1419a (step S2). Then, the CPU 1419b serves to synthesize the one-dimensional image data g(x) into the two-dimensional image data G(g(x), y) per one line and store the two-dimensional image data G(g(x), y) in the first line area of the image memory 1419c (step S3).

The CPU 1419b serves to increment a counter y indicating a y-coordinate address (step S4) and repeat the foregoing process until the counter y reaches a predetermined maximum value (maximum movement) set for the finger F (step S5).

When the counter y is counted up, the CPU 1419b reads out the two-dimensional image data G(g(x), y) of the image memory 1419c and outputs the data to the identifying device (not shown).

As shown in FIG. 28, hence, in case the finger F is moved from the roller 1413 to the lighting device 1415 (+y-axis direction) in contact with the roller 1413, the one-dimensional image data g(x) per each line of the fingerprint pattern are sequentially stored in the line buffer 1419a, and the two-dimensional image data G(g(x), y) of the fingerprint pattern are synthesized in sequence from the data corresponding to the tip of the finger and stored in the image memory 1419c.

The line image sensor 1418 of FIG. 28 has a reading accuracy r as an x-axis unit. The image memory 1419c has a minimum sensing amount s of the rotary encoder 1416 as a +y-axis unit.

As shown in FIG. 29, when the finger F is moved from the lighting device 1415 to the roller 1413 (−y-axis direction) in contact with the roller 1413, that is, the finger F is moved on the slit 1414 from the second joint to the first joint, the rotary encoder 1416 serves to output to the CPU 1419b the y-coordinate signal consisting of a pulse for each minimum sensing among s and a negative (−y) rotating direction signal.

The fingerprint surface of the finger F is lit up by the lighting device 1415. The light reflected on the fingerprint surface passes through the slit 1414 and is shaped into parallel rays of light through the effect of the cylindrical lens 1417. The resulting parallel rays of light are read by the line image sensor 1418. The one-dimensional image data g(x) of the fingerprint pattern per one line are sequentially stored in the line buffer 1419a. That is, the one-dimensional image data g(x) of the fingerprint pattern are read in the direction of the second joint to the first joint of the finger F. Hence, the image data g(x) are stored in the line buffer 1419a per each line.

As shown in FIG. 27, when the CPU 1419b receives the y-coordinate signal from the rotary encoder 1416 (step S1), the CPU 1419b instructs to read the one-dimensional image data g(x) per one line stored in the line buffer 1419a (step S2). The two-dimensional image data G(g(x), y) per one line are synthesized from the one-dimensional image data g(x) and are stored in the first line area of the image memory 1419c (step S3). That is, in response to the negative rotating direction signal from the rotary encoder 1416, the CPU 1419b instructs to store the two-dimensional image data G(g(x), y) in sequence from the y-axis maximum value address of the image memory 1419c to the minimum value address area.

Then, the counter y for the y-coordinate address is incremented (step S4). Then, the foregoing process is repeated until the counter y reaches a predetermined maximum value (maximum movement) set for the finger F (step S5).

When the counter y is counted up, the CPU 1419b instructs the image memory 1419c to read the two-dimensional image data G(g(x), y) and outputs the data to the identifying device (not shown).

As shown in FIG. 29, hence, in case the finger F is moved on the slit 1414 from the second joint to the first joint, like the reverse movement, the normal two-dimensional image data G(g(x), y) of the fingerprint pattern are stored in the image memory 1419c.

The present embodiment is capable of enhancing a collating accuracy of the fingerprint by securing more read data. That is, as shown in FIGS. 28 and 29, since the finger F is allowed to move to and fro, the embodiment is capable of respectively reading and synthesizing the two-dimensional image data G(g(x), y) on the forward travel (+y-axis direction) and the backward travel (−y-axis direction) of the finger F for the purpose of enhancing the collating accuracy of the fingerprint.

In this case, all the two-dimensional images are not required to be synthesized on the forward and backward travels of the finger F. The present embodiment may be constructed to synthesize the two-dimensional image, assuming that the rotary encoder 1416 outputs a positive pulse and then three negative pulses as a result of changing the rotating direction of the roller 1413 (from +y-axis to −y-axis direction).

The present embodiment makes it possible to input the fingerprint pattern through the slit 1414 without having to contact the finger F to the fingerprint input base 1411. Hence, the resulting image is subject to no adverse effect by the residual fingerprint. Further, The reading accuracy per one pixel depends on the minimum sensing amount s of the rotary encoder 1416 and the reading accuracy r of the line image sensor 1418. Hence, with the simple arrangement, the embodiment is capable of realizing the reading accuracy of about 50 μm per one pixel.

With the simple arrangement, therefore, the present embodiment makes is possible to positively input the fingerprint pattern with no adverse effect caused by the residual fingerprint.

Figure 30:
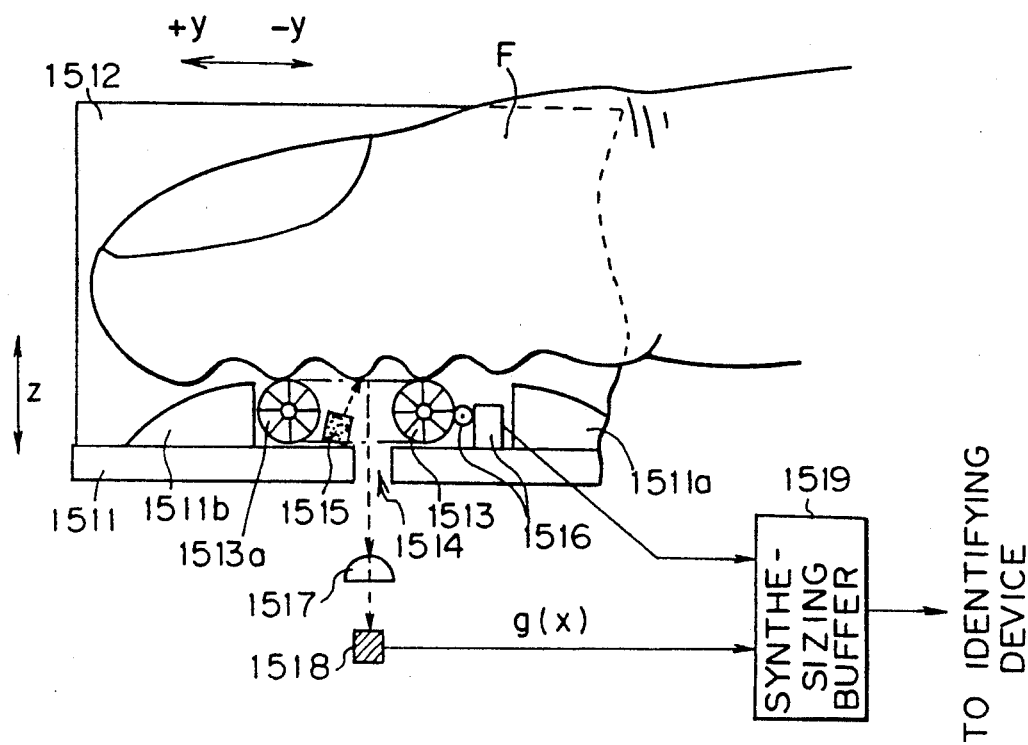
FIG. 30 is a schematic diagram showing a fingerprint input apparatus according to a second embodiment of the fifth invention.
Figure 31:
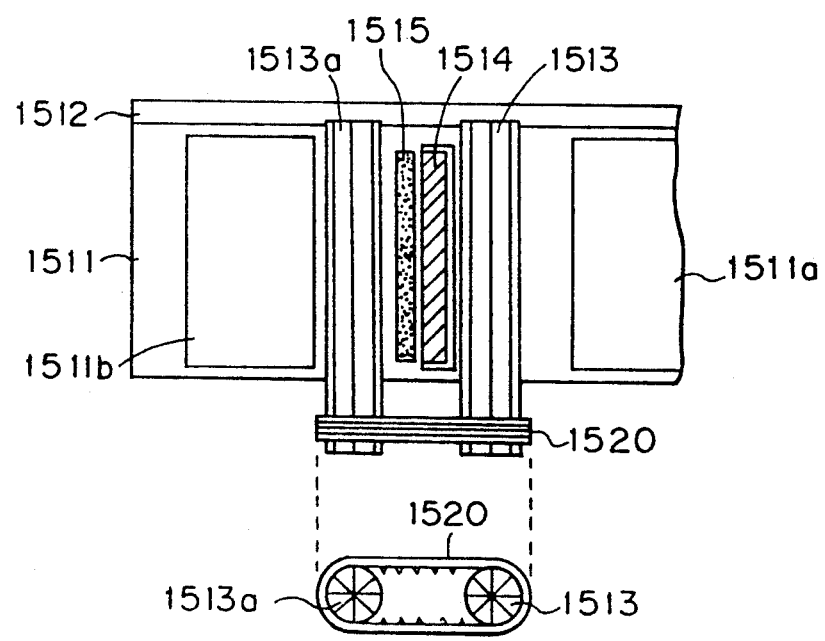
FIG. 31 is a plane view showing an essential portion of the fingerprint input apparatus shown in FIG. 30.

FIG. 30 is a diagram schematically showing a second embodiment of the fifth invention. FIG. 31 is a plane view showing an essential portion of the fingerprint input apparatus of FIG. 30.

With reference to FIGS. 30 and 31, the fingerprint input apparatus according to the second embodiment of the fifth invention includes a fingerprint input base 1511, guides 1511a and 1511b, a guide plate 1512, a roller 1513 and 1513a, a slit 1514, a lighting device 1515, a rotary encoder 1516, a cylindrical lens 1517, a line image sensor 1518, a synthesizing buffer 1519, and a timing belt 1520.

The construction of the second embodiment has the same components as that of the first embodiment, except the guides 1511a and 1511b, the roller 1513a, and the timing belt 1520.

The rollers 1513 and 1513a, and the lighting device 1515 are horizontally located on the fingerprint input base 1511 in a manner that the lighting device 1515 is located between the rollers 1513 and 1513a. As shown in the lower part of FIG. 31, the rollers 1513 and 1513a are allowed to rotate together in the same direction through the effect of the timing belt 1520.

The timing belt 1520 may be replaced with a gear or the like.

The guides 1511a and 1511b are respectively located on the upstream side (−y direction as viewed in FIG. 30) of the roller 1513 and the downstream side (+y direction as viewed in FIG. 31) of the roller 1513a provided on the fingerprint input base 1511. The guides 1511a and 1511b are convexed in section in a manner to allow the finger F to move slidably on the rollers 1513 and 1513a.

Like the first embodiment, the synthesizing buffer 1419 provides the line buffer 1419a, the CPU 1419b, and the image memory 1419c shown in FIG. 26.

The fingerprint input apparatus according to the second embodiment of the fifth invention operates in a similar to the apparatus according to the first embodiment.

The foregoing first embodiment is constructed so that the finger F is moved on one roller 1413. If, therefore, the finger tip is vertically slipped (in the z-axis direction as viewed in FIG. 30), the read image data may lower the accuracy. On the other hand, the second embodiment is constructed so that the fingerprint surface of the finger F is allowed to horizontally move with the rollers 1513, 1513a and the guides 1511a, 1511b, resulting in being able to improve the reading accuracy of the fingerprint pattern.

Figure 32:
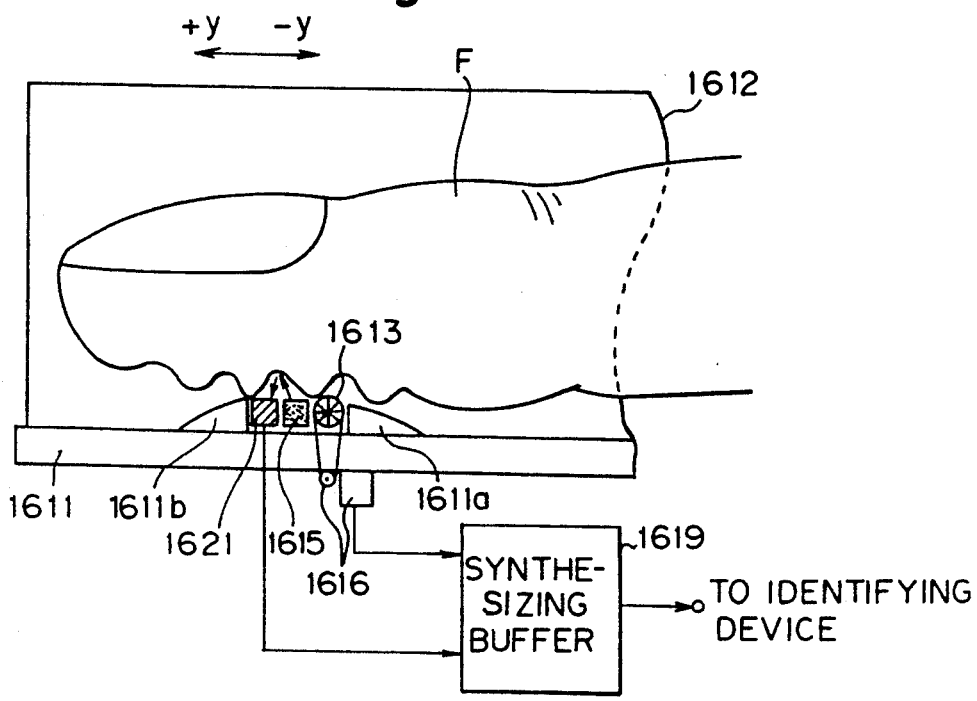
FIG. 32 is a schematic diagram showing a fingerprint input apparatus according to a third embodiment of the fifth invention.

FIG. 32 is a diagram schematically showing the fingerprint input apparatus according to a third embodiment of the fifth invention.

As shown in FIG. 32, the fingerprint input apparatus according to the third embodiment of the fifth invention includes a fingerprint input base 1611, guides 1611a and 1611b, a guide plate 1612, a roller 1613, a lighting device 1615, a rotary encoder 1616, and a synthesizing buffer 1619.

The present embodiment provides a close-contact type image sensor 1621 which allows the fingerprint surface of a finger F to be slid in place of the roller 1513a, the slit 1514, the cylindrical lens 1517, the line image sensor 1518, and the timing belt 1520.

The close-contact image sensor 1621 is located on the downward side (+y direction as viewed in FIG. 32) of the lighting device 1615 provided on the fingerprint input base 1611.

The other components of the present embodiment are same as those of the first and the second embodiments.

Like the first embodiment of the fifth invention, the synthesizing buffer 1619 provides the line buffer 1419a, the CPU 1419b, and the image memory 1419c as shown in FIG. 26.

The fingerprint input apparatus according to the third embodiment operates in a similar manner to those of the first and the second embodiments, except the function of the close-contact image sensor 1621. That is, the fingerprint surface is lit up by the lighting device 1615 and the light reflected on the fingerprint surface is directly picked up by the close-contact image sensor 1621. Then, the fingerprint pattern is sequentially stored as one-dimensional image data g(x) per one line in the line buffer 1419a. The subsequent operation is executed in a similar manner to that of the first embodiment.

The first and the second embodiments take the steps of guiding the light reflected on the fingerprint surface of the finger F through the slit 1414 or 1514, parallelizing the light through the cylindrical lens 1417 or 1517, sending the parallelized light to the line image sensor 1418 or 1518. Hence, the light travels a long distance. On the other hand, the third embodiment is constructed to read the fingerprint pattern of the finger F with only the close-contact image sensor 1621. It results in being able to reduce the fingerprint input apparatus according to the third embodiment in size as compared with the apparatus according to the first and the second embodiments.

Figure 33:
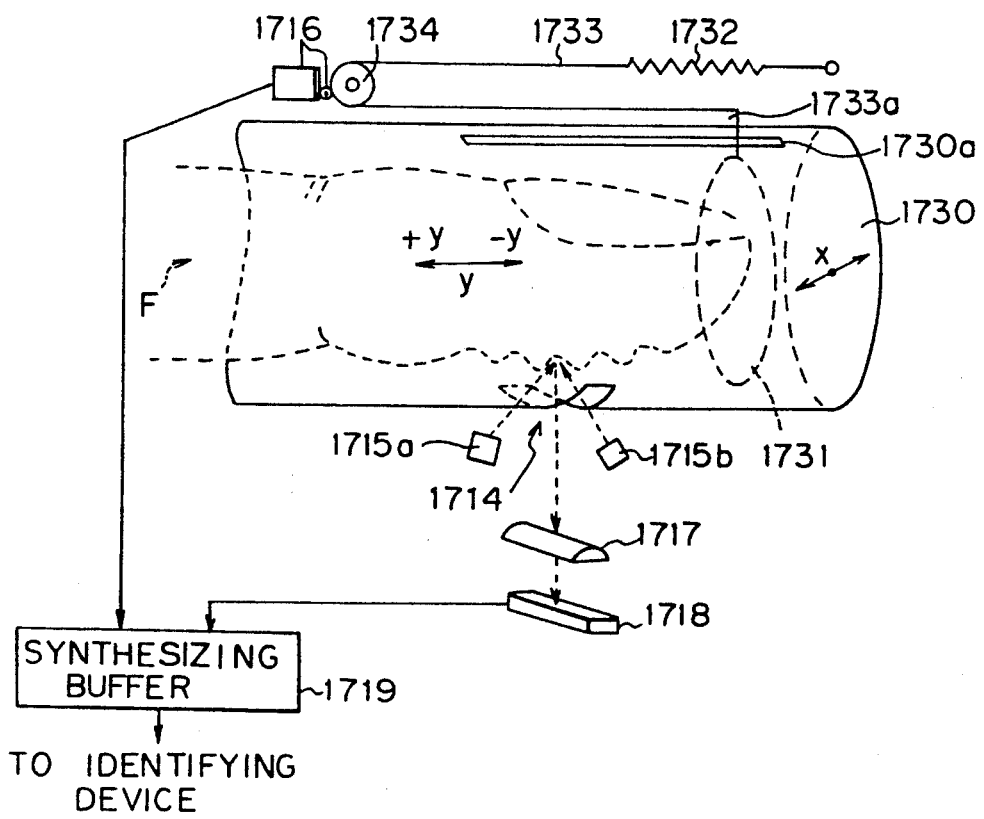
FIG. 33 is a schematic diagram showing a fingerprint input apparatus according to a first embodiment of a sixth invention.

FIG. 33 is a diagram schematically showing a fingerprint input apparatus according to a first embodiment of a sixth invention.

As shown in FIG. 33, the fingerprint input apparatus according to the first embodiment of the sixth invention includes a slit 1714, lighting devices 1715a and 1715b, a rotary encoder 1716, a cylindrical lens 1717, a line image sensor 1718, a synthesizing buffer 1719, a cylindrical guide 1730, a disc 1731, a coil spring 1732, a belt 1733, and a pulley 1734.

The present fingerprint input apparatus provides the cylindrical guide 1730 horizontally located in a manner to allow the finger F to be inserted. The cylindrical guide 1730 has the substantially same inner diameter as the outer diameter of a finger F.

Inside of the cylindrical guide 1730 is provided the disc 1731 whose diameter is substantially same as inner diameter of the cylindrical guide 1730. The disc 1731 is located in a vertical manner to the movement of the finger F (y-axis direction as viewed in FIG. 33).

The disc 1731 is linked with the coil spring 1732 through the belt 1733. That is, the belt 1733 is wound around the pulley 1734 located outside of the cylindrical guide 1730. 1733a denotes a part of the belt 1733 extending from the pulley 1734 to the disc 1731. The part 1733a is made of a hard material. The part 1733a passes through a through-groove 1730a formed on the cylindrical guide 1730 and is linked with the coil spring 1732.

The disc 1731 is allowed to move in the axial direction (y-axis direction as viewed in FIG. 33) of the cylindrical guide 1730. That is, the disc 1731 is forced to be pulled into an opposite direction to the finger-inserting direction (−y-axis direction as viewed in FIG. 33) by means of the coil spring 1732 located outside of the cylindrical guide 1730.

The pulley 1734 is linked to the rotary encoder 1716.

When the finger F is inserted into the cylindrical guide 1730, the tip of the finger F pushes the disc 1731 against the pulling force of the coil spring 1732, thereby moving the disk 1731 and the belt 1733. It results in allowing the rotary encoder 1716 to sense the amount of the movement of the finger F in the −y-axis direction.

The other components of the first embodiment of the sixth invention are same as those of the first to the third embodiments of the fifth invention.

The slit 1714 is formed on the substantially center of the lower side of the cylindrical guide 1730.

The lighting devices 1715a and 1715b, the cylindrical lens 1717, and the line image sensor 1718 are provided below the slit 1714. When the finger F is inserted into the cylindrical guide 1730, the fingerprint surface of the finger F is lit up through the slit 1714 by the lighting devices 1715a and 1715b. The light reflected on the fingerprint pattern of the finger F is received and parallelized through the cylindrical lens 1717. Then, the parallelized light is directly picked up by the line image sensor 1718.

The rotary encoder 1716 outputs to the synthesizing buffer 1719 the sensing signal of the amount of the movement and the moving direction of the finger F. The line image sensor 1718 also outputs a reading signal to the synthesizing buffer 1719. Depending on these signals, the synthesizing buffer 1718 serves to synthesize the two-dimensional image data G(g(x),y) as shown in FIGS. 28 and 29.

The rotary encoder 1716 provides a minimum sensing amount s of about 50 μm per one pixel. The line image sensor 1718 also provides a reading accuracy r of about 50 μm per one pixel.

The synthesizing buffer 1719 is connected to an identifying device (not shown) for identifying the input fingerprint pattern.

Like the first embodiment of the fifth invention, the synthesizing buffer 1719 provides the line buffer 1419a, the CPU 1419b, and the image memory 1419c as shown in FIG. 26.

The fingerprint input apparatus according to the first embodiment of the sixth invention operates in a similar manner to the apparatus according to the first embodiment of the fifth invention.

The present embodiment is capable of enhancing a collating accuracy of the fingerprint by securing more read data. That is, as shown in FIGS. 28 and 29, since the finger F is allowed to move to and fro, the embodiment is capable of respectively reading and synthesizing the two-dimensional image data G(g(x), y) on the forward travel (+y-axis direction) and the backward travel (−y-axis direction) of the finger F for the purpose of enhancing the collating accuracy of the fingerprint.

In this case, all the two-dimensional images are not required to be synthesized on the forward and backward travels of the finger F. The present embodiment may be constructed to synthesize the two-dimensional image, assuming that the rotary encoder 1416 outputs a positive pulse and then three negative pulses as a result of changing the rotating direction of the roller 1413 (from −y-axis to +y-axis direction).

As mentioned above, the present embodiment provides the cylindrical guide 1730 having the substantially same inner diameter as the outer diameter of the finger F, thereby disallowing the finger F to be slipped laterally (x-axis direction as viewed in FIG. 33). Further, the present embodiment has a capability of inputting a fingerprint pattern through the slit 1714. Hence, no adverse effect of the residual fingerprint is brought about on the resulting fingerprint image. The reading accuracy per one pixel depends on the minimum sensing amount s of the rotary encoder 1416 and the reading accuracy r of the line image sensor 1418. Hence, with the simple arrangement, the embodiment is capable of realizing the reading accuracy of about 50 $\mu$m per one pixel.

Accordingly, the fingerprint input apparatus according to the first embodiment of the sixth invention is capable of accurately inputting the fingerprint pattern with no adverse effect of the residual fingerprint.

Figure 34:
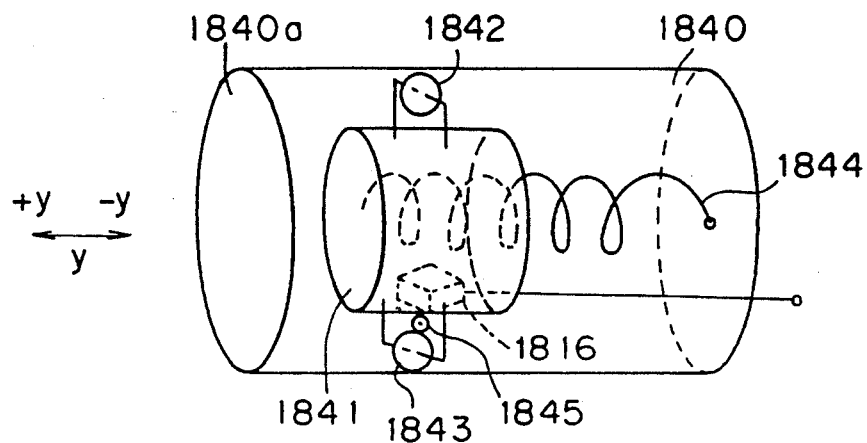
FIG. 34 is a schematic diagram showing an essential portion of the fingerprint input apparatus according to a second embodiment of the sixth invention.
Figure 35:
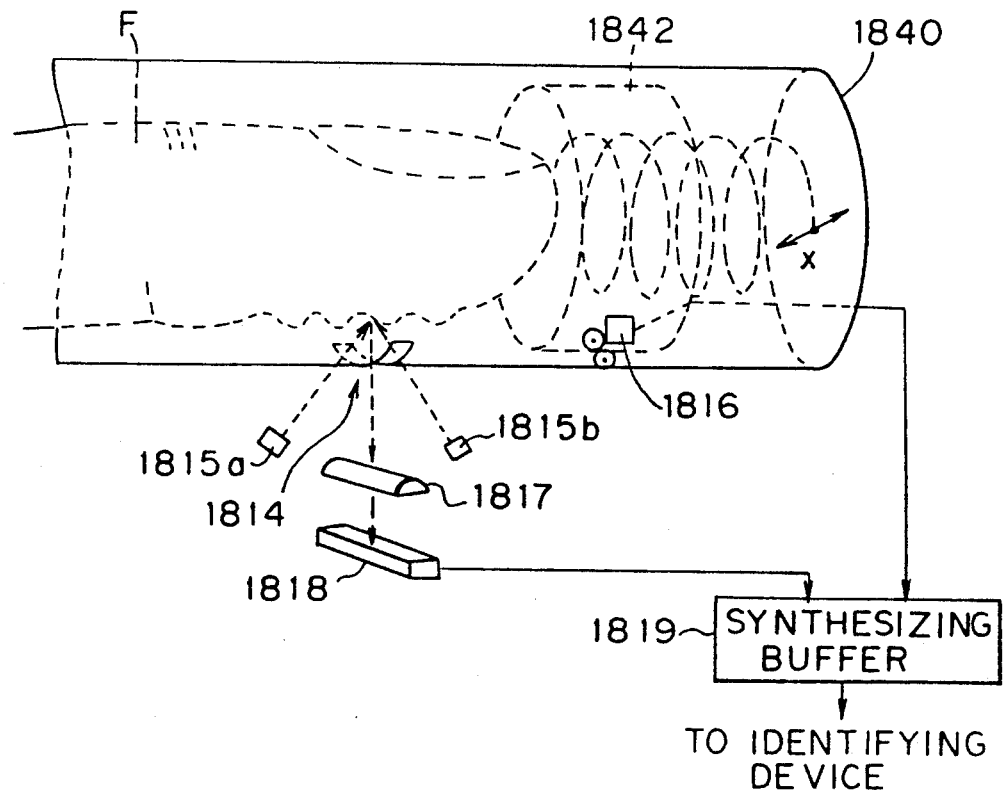
FIG. 35 is a schematic diagram showing overall construction of the fingerprint input apparatus shown in FIG. 34.

FIG. 34 is a diagram schematically showing an essential portion of a fingerprint input apparatus according to a second embodiment of the sixth invention. FIG. 35 is a diagram schematically showing the overall construction of the fingerprint input apparatus.

As shown in FIGS. 34 and 35, the present fingerprint input apparatus includes a slit 1814, lighting devices 1815a and 1815b, a rotary encoder 1816, a cylindrical lens 1817, a line image sensor 1818, a synthesizing buffer 1819, a cylindrical guide 1840, a cylindrical member 1841, rollers 1842 and 1843, a coil spring 1844, and a roller 1845.

As is understood from the above description, the present embodiment provides the cylindrical guide 1840 having an end wall located on the opposite side (−y-axis direction as viewed in FIG. 34) to a finger-inserting opening 1840a in place of the cylindrical guide 1730, the disc 1731, the coil spring 1732, the belt 1733, and the pulley 1734. The cylindrical guide 1840 having the substantially same size as the cylindrical guide 1730 included in the first embodiment of the sixth invention.

Inside of the cylindrical guide 1840 is provided the cylindrical member 1841, inside of which the rotary encoder 1816 is fixed.

The cylindrical member 1841 is allowed to move in the axial direction (y-axis direction as viewed in FIG. 34) inside of the cylindrical guide 1840 through the rollers 1842 and 1843 provided on the upper end and the lower end of the cylindrical member 1841 itself. The cylindrical member 1841.is linked with the end wall of the cylindrical guide 1840 through the coil spring 1844 so that it is forced to be pulled in the opposite direction (+y-axis direction) to the finger-inserting direction (−y-axis direction) by means of the coil spring 44.

The roller 1843 located on the lower end is linked with the rotary encoder 1816 provided inside of the cylindrical member 1841 through the roller 1845. When, therefore, the finger F is inserted into the cylindrical guide 1840 and the finger tip pushes the cylindrical member 1841 against the pulling force of the coil spring 1844, the cylindrical member 1841 is moved in concert with the rotary encoder 1816. Hence, the rotary encoder 1816 is capable of sensing the amount of the movement and the moving direction of the finger F.

The other essential components of the present embodiment is same as those of the first to the third embodiments of the fifth invention.

Like the first embodiment of the fifth invention, the synthesizing buffer 1819 provides the line buffer 1419a, the CPU 1419b, and the image memory 1419c as shown in FIG. 26.

The fingerprint input apparatus according to the second embodiment of the sixth invention operates in a similar manner to the apparatus according to the first embodiment of the fifth invention.

As mentioned above, the present embodiment provides the cylindrical guide 1840 having the substantially same inner diameter as the outer diameter of the finger F, thereby disallowing the finger F to be slipped laterally (x-axis direction as viewed in FIG. 35). Further, the present embodiment has a capability of inputting a fingerprint pattern through the slit 1814. Hence, no adverse effect of the residual fingerprint is brought about on the resulting fingerprint image. The reading accuracy per one pixel depends on the minimum sensing amount s of the rotary encoder 1816 and the reading accuracy r of the line image sensor 1818. Hence, with the simple arrangement, the embodiment is capable of realizing the reading accuracy of about 50 $\mu$m per one pixel.

Accordingly, the fingerprint input apparatus according to the second embodiment of the sixth invention is capable of accurately inputting the fingerprint pattern with no adverse effect of the residual fingerprint.

In turn, the description will be directed to the seventh invention.

Figure 36:
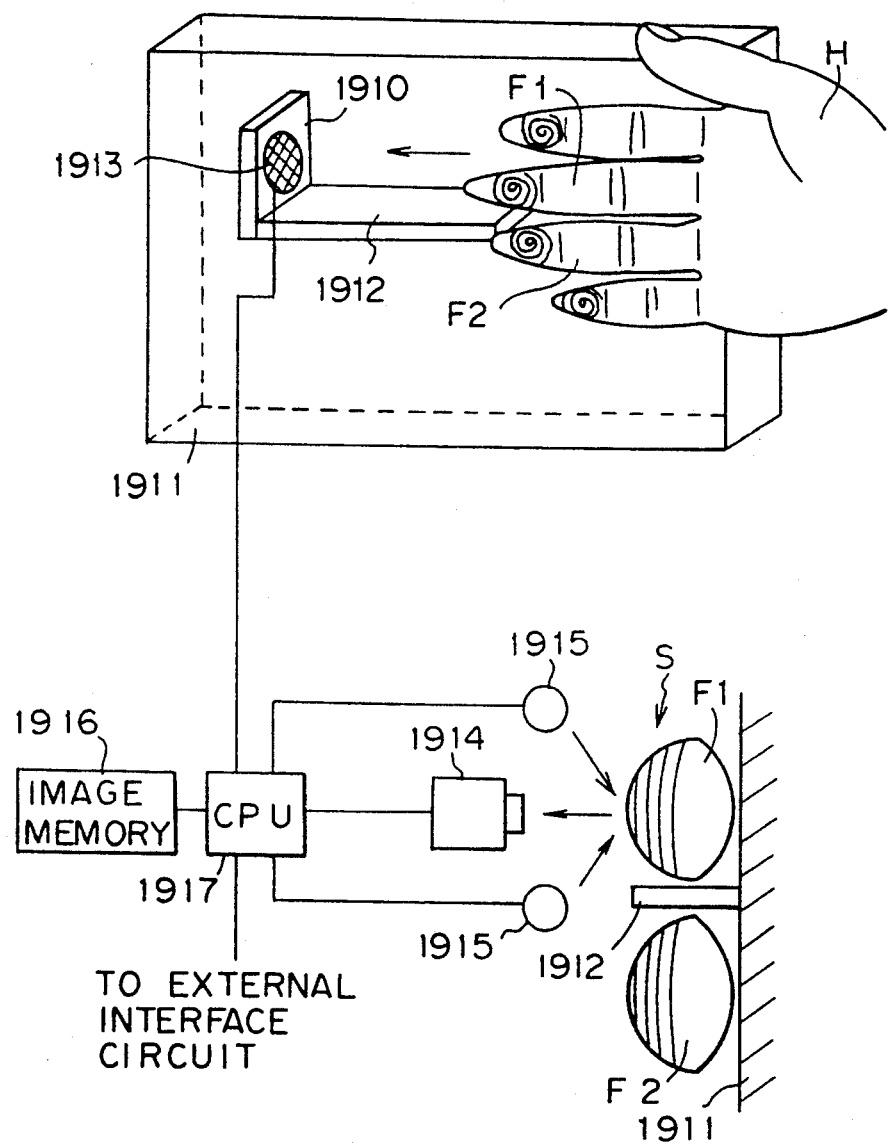
FIG. 36 is a schematic diagram showing a fingerprint input apparatus according to a first embodiment of a seventh invention.

FIG. 36 is a schematic diagram showing a fingerprint input apparatus according to a first embodiment of a seventh invention.

As shown in FIG. 36, the fingerprint input apparatus according to the present embodiment includes a touch plate 1910, a supporting plate 1911, a finger guide 1912, a sensor 1913, an image pickup device 1914, a lighting device 1915, an image memory 1916, and a CPU 1917.

The supporting plate 1911 is placed upright in a manner that it is in contact with the back of a hand H, that is, an opposite side of a fingerprint surface S for supporting the hand.

The tabular finger guide 1912 is provided on the supporting plate 1911 horizontally and perpendicular to the side of the supporting plate 1911. The tabular finger guide 1912 is allowed to be laid between the a subject finger F1 from which the fingerprint is to be picked up and the adjacent finger F2.

The touch plate 1910 is formed on the side of the supporting plate 1911 perpendicular to the finger guide 1912. The finger F1 is allowed to contact the touch plate 1911 when the finger F1 is moved along the finger guide 1912. The touch plate 1910 provides the sensor 1913 for sensing whether or not the finger F1 is located at a predetermined input reading location of the finger guide 1912 when the finger F1 is being moved toward the arrow as viewed in FIG. 36.

That is, the fingerprint input apparatus according to the present embodiment is constructed so that the fingerprint surface S of the finger F1 is guided with the surface S directed to the opposite side to the side of the supporting plate 1911.

At the predetermined input reading location of the finger guide 1912, there is located the lighting device 1915 and the image pickup device 1914 in opposition to the fingerprint surface S and the supporting plate 1911. The lighting device 1915 serves to uniformly light up the fingerprint surface S of the finger F1. The image pickup device 1914 serves to image the fingerprint pattern on the basis of the light reflected on the fingerprint surface S lit by the lighting device 1915.

The image pickup device 1914 includes a lens for focusing the light reflected on the fingerprint pattern of the fingerprint surface S lit by the lighting device 1915 and a two-dimensional image sensor such as a charge-coupled device. The lighting device 1915 may be composed of a circular fluorescent tube. In addition, the image pickup device 1914 is located so that it is focused on the imaginary location of the fingerprint surface S.

The CPU 1917 is connected to the sensor 1913, the lighting device 1915, the image memory 1916 for storing an image data representing the fingerprint pattern, and an external interface circuit (not shown).

Next, the operation of the present embodiment will be described.

As shown in FIG. 36, the subject finger F1 and the adjacent finger F2 are moved toward the arrow in a manner to allow the finger guide 1912 to be laid between both fingers. When the finger F1 reaches the predetermined input reading location, the sensor 1913 operates to sense the finger F1. The finger guide 1912 serves to restrict the lateral (vertical) slippage of the fingerprint surface S of the finger F1. The side of the vertically-located supporting plate 1911 and the finger guide 1912 serve to restrict the turning slippage of the fingerprint surface S. The movement of the fingerprint S toward the arrow is restricted by the sensor 1913 formed on the touch plate 1910.

When the sensor 1913 senses the finger F1 at the predetermined input reading location, the sensor 1913 sends out a sensing signal to the CPU 1917. In response to the sensing signal, the CPU 1917 serves to actuate the lighting device 1915 and output an imaging-start signal to the image pickup device 1914. The image pickup device 1914 serves to image the fingerprint pattern depending on the light reflected on the fingerprint surface S lit by the lighting device 1915. The CPU 1917 serves to control the write of the fingerprint-pattern image picked up by the image pickup device 1914 into the image memory 1916.

The present embodiment, therefore, is capable of inputting the fingerprint pattern without having to contact the fingerprint surface on a glass plate or the like, thereby overcoming the adverse effect of the residual fingerprint.

As mentioned above, the lateral (vertical) slippage of the fingerprint surface S of the finger F1 is restricted by the finger guide 1912. The turning slippage of the fingerprint surface S is restricted by the side of the supporting plate 1911 and the finger guide 1912. The movement of the fingerprint surface S toward the arrow is restricted by the sensor 1913. Hence, the present embodiment is capable of positively and easily positioning the finger-pattern image, thereby allowing the fingerprint pattern to be reliably input.

Those advantages make contribution to enhancing the efficiency of collating and identification of a fingerprint.

Further, the above description about the present embodiment has concerned with the apparatus which is capable of inputting the fingerprint pattern of the finger of a right hand. For constructing the fingerprint input apparatus capable of inputting a fingerprint pattern of a finger of a left hand, it is possible to provide the touch plate, the finger guide, and the sensor on the opposite side to the side of the supporting plate 1911 on which the touch plate 1910, the finger guide 1912, and the sensor 1913 are provided and locate the image pickup device and the lighting device at the opposite places.

Figure 37:
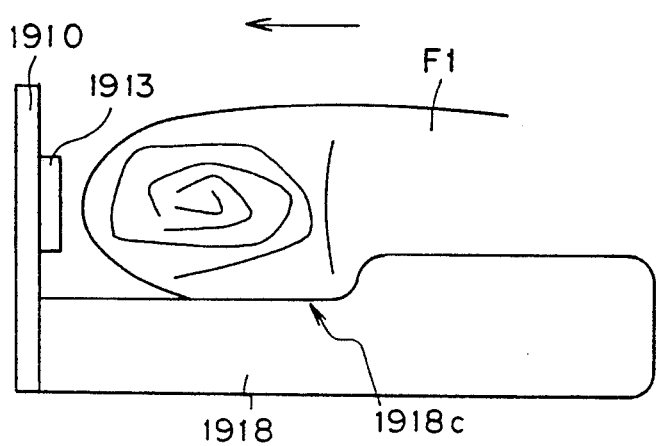
FIG. 37 is a side view showing transformation of a finger guide included in the fingerprint input apparatus shown in FIG. 36.
Figure 38:
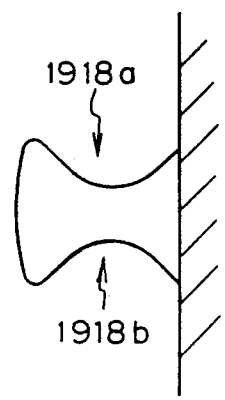
FIG. 38 is a section showing the finger guide shown in FIG. 37.

FIG. 37 is a plane view schematically showing a transformation of the finger guide included in the fingerprint input apparatus shown in FIG. 36. FIG. 38 is a side view showing the right side of the transformation of the finger guide.

As shown in FIGS. 37 and 38, 1918 denotes a finger guide corresponding to the finger guide 1912 of the fingerprint input apparatus shown in FIG. 36. The finger guide 1918 provides a groove 1918a and a groove 1918b along the moving direction of the subject finger F1 (toward the arrow). The groove 1918a is used for sliding the side of the subject finger F1 therethrough. The groove 1918b is used for sliding the side of the finger F2 therethrough.

These grooves 1918a and 1918b are smoothed so as to suit to the form of the fingers F1 and F2.

The finger guide 1918 provides a cut-away 1918c formed on the predetermined input reading location in a manner to allow the fingerprint surface of the finger F1 to be seen from the outside.

The finger guide 1918 thus serves to define the distance between the fingerprint surface and the image pickup device (not shown) with the grooves 1918a and 1918b. It results in allowing the image pickup device and a lighting device (not shown) to pick up a vivid image of a fingerprint pattern. It means that the present embodiment is capable of positively inputting the fingerprint pattern without having to contact the finger with the glass plate or the like.

Figure 39:
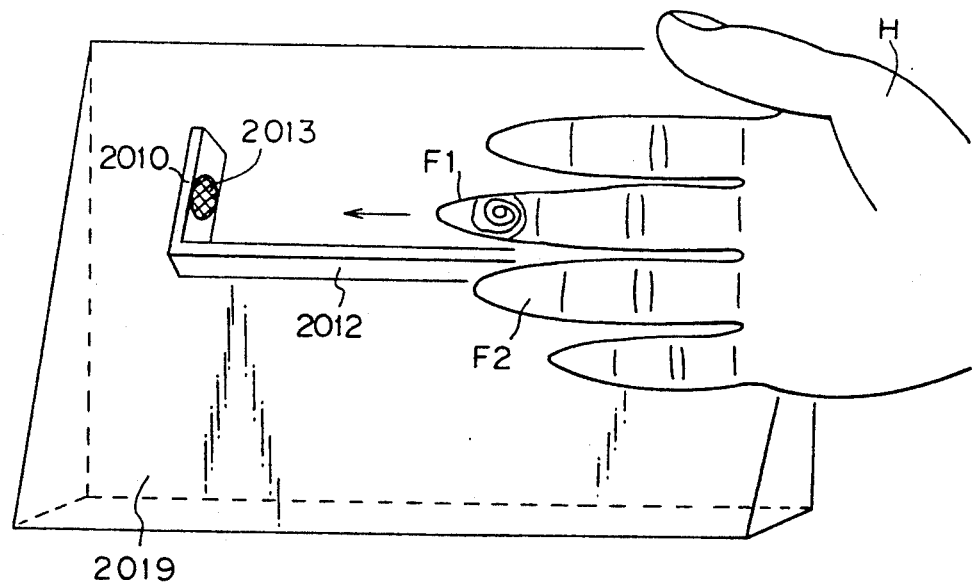
FIG. 39 is a perspective view showing a fingerprint input apparatus according to a second embodiment of the seventh invention.
Figure 40:
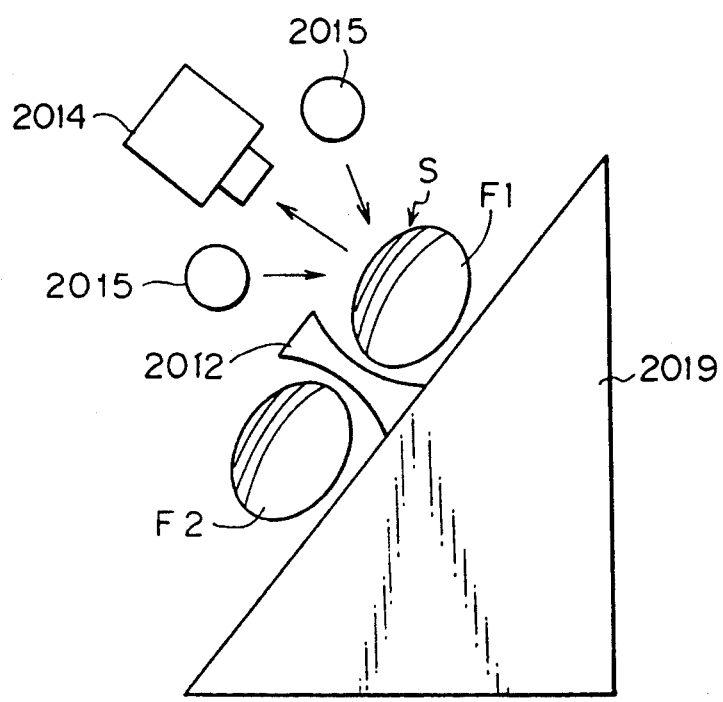
FIG. 40 is a side view showing the fingerprint input apparatus shown in FIG. 39.

FIG. 39 is a perspective view showing schematic arrangement of a fingerprint input apparatus according to a second embodiment of the seventh invention. FIG. 40 is a side view showing the fingerprint input apparatus shown in FIG. 39.

As shown in FIGS. 39 and 40, the fingerprint input apparatus according to the present embodiment includes a touch plate 2010, a supporting plate 2019, a finger guide 2019, a sensor 2013, an image pickup device 2014, a lighting device 2015, an image memory (not shown), and a CPU (not shown). The present embodiment basically operates in a similar manner to the first embodiment of the seventh invention.

Unlike the supporting plate 1911 shown in FIG. 36, the side of which is located vertically, the present embodiment provides the supporting plate 2019, the side of which is formed at a predetermined angle with the vertical plane. The supporting plate 2019 provides on the side the touch plate 2010, the finger guide 2012, and the sensor 2013. With the movement of the finger F1 along the finger guide 2012, the fingerprint surface S is directed obliquely upward.

According to the present embodiment, the back of a hand H is moved along the supporting plate 2011 in a manner to allow the finger guide 2012 to be laid between the subject finger F1 and the adjacent finger F2. The fingerprint surface S is moved in the moving direction of the finger (toward the arrow) with the surface S being directed obliquely upward. It is natural for a user to input the fingerprint pattern.

As shown in FIG. 40, the fingerprint surface S is located obliquely downward to the image pickup device 2014. The location makes contribution to enhancing the dustproof effect on the lens provided in the image pickup device 2014.

Further, the present embodiment is capable of inputting the fingerprint pattern without having to contact the finger on anywhere, resulting in allowing the fingerprint pattern to be positively input with no adverse effect of the residual fingerprint.

Accordingly, those functions make great contribution to enhancing the efficiency of collating and identifying the fingerprint.

The angle between the side of the supporting plate 2019 and the vertical plane is defined so that the user can feel natural in moving his or her finger along the finger guide.

The above description about this embodiment has been concerned with the fingerprint input apparatus dedicated for a right hand. For constructing the apparatus dedicated for a left hand, it is possible to provide the touch plate, the finger guide, and the sensor on the opposite side and locate the image pickup device and the lighting device at the opposite places.

Figure 41:
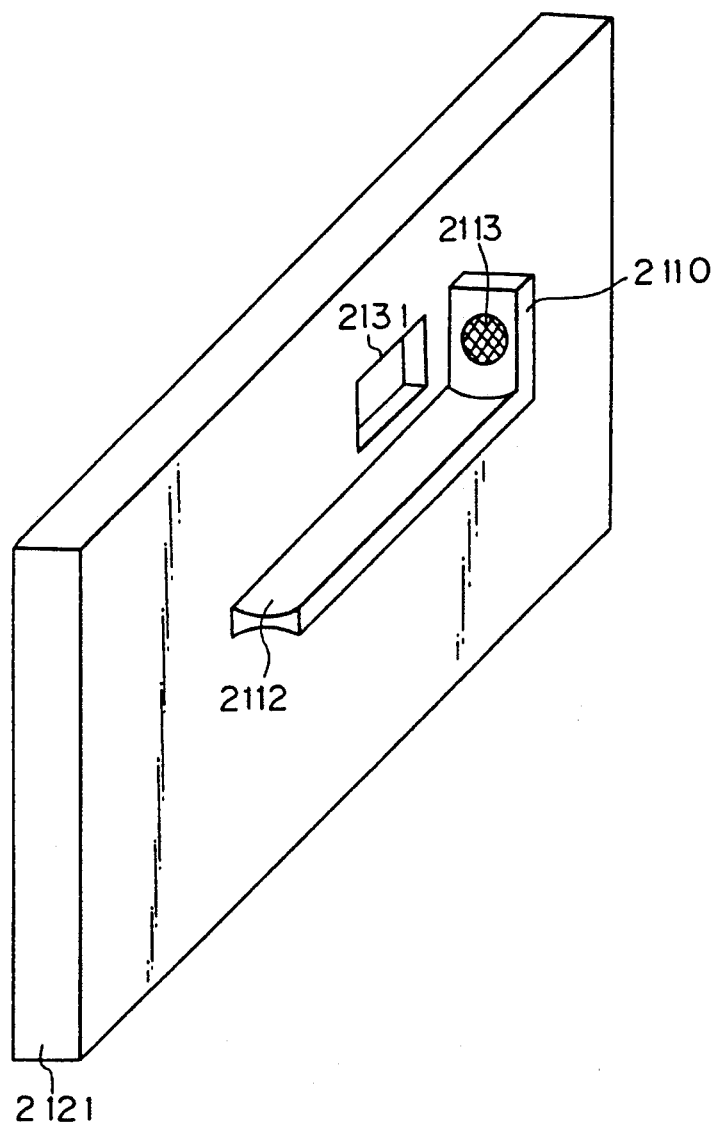
FIG. 41 is a perspective view showing a fingerprint input apparatus according to a third embodiment of the seventh invention.
Figure 42:
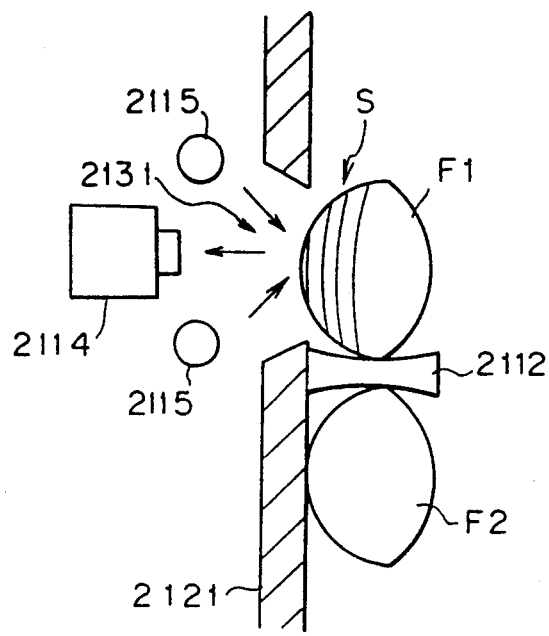
FIG. 42 is a side view showing the fingerprint input apparatus shown in FIG. 41.

FIG. 41 is a perspective view showing schematic construction of a fingerprint input apparatus according to a third embodiment of the seventh invention. FIG. 42 is a side view showing the fingerprint input apparatus shown in FIG. 41.

As shown in FIGS. 41 and 42, the fingerprint input apparatus according to the present embodiment includes a touch plate 2110, a supporting plate 2121, a finger guide 2112, a sensor 2113, an image pickup device 2114, a lighting device 2115, an image memory (not shown), and a CPU (not shown). The present embodiment basically operates in a similar manner to the first embodiment of the seventh invention.

According to the foregoing first and second embodiment, the supporting plates 1911 and 2019 are located so as to contact the back of the hand H, that is, the opposite side of the fingerprint surface S. On the other hand, the present embodiment provides the supporting plate 2121 which is located to contact the palm of the hand H, that is, the fingerprint surface S itself and support it.

The supporting plate 2121 provides a through hole 2131 formed thereon. The image pickup device 2114 enables to read the fingerprint pattern through the through hole 2131 as shown in FIG. 42. Hence, the fingers F1 and F2 are located on the respective sides of the supporting plate 2121.

According to the present embodiment, the palm of the hand is moved along the supporting plate 2121 in a manner to allow the finger guide 2112 to be laid between the subject finger F1 and the adjacent finger F2. Hence, it is natural for a user to input the fingerprint pattern.

Further, the present embodiment is capable of inputting the fingerprint pattern without having to contact the finger on anywhere, resulting in allowing the fingerprint pattern to be positively input with no adverse effect of the residual finger.

The above description about the present embodiment has concerned with the fingerprint input apparatus dedicated for a right hand. For constructing the apparatus dedicated for a left hand, it is possible to provide the touch plate, the finger guide, and the sensor on the opposite side and locate the image pickup device and the lighting device at the opposite locations.

Figure 43A:
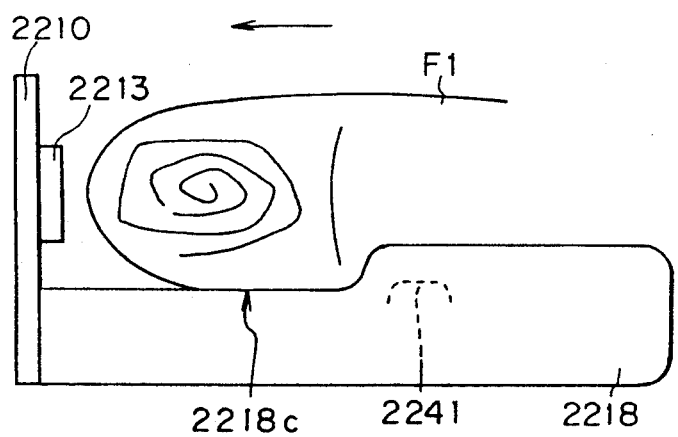
FIG. 43A is a side view showing the fingerprint input apparatus shown in FIGS. 37 and 38 providing a mechanical sensor for sensing whether or not a finger guide is clipped by a subject finger and its adjacent finger.
Figure 43B:
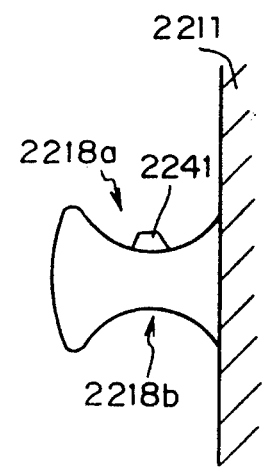
FIG. 43B is a section showing the construction shown in FIG. 43A.

FIG. 43A is a plane view showing the fingerprint input apparatus shown in FIGS. 37 and 38 providing a mechanical sensor 2241 served as a sensor for sensing whether or not the finger guide 2218 is located between the subject finger and the adjacent finger. FIG. 43B is a side view showing the right side of the essential portion of the fingerprint input apparatus.

Figure 44A:
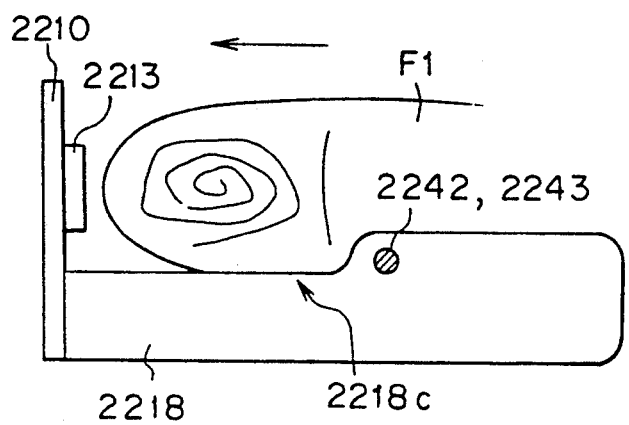
FIG. 44A is a plane view showing the fingerprint input apparatus shown in FIGS. 37 and 38 providing optical sensors for sensing whether or not a finger is moved to a predetermined location along a finger guide.
Figure 44B:
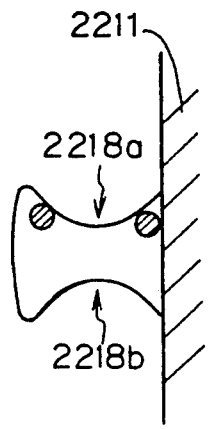
FIG. 44B is a side view showing the right side of the fingerprint input apparatus of FIG. 44A.
Figure 44C:
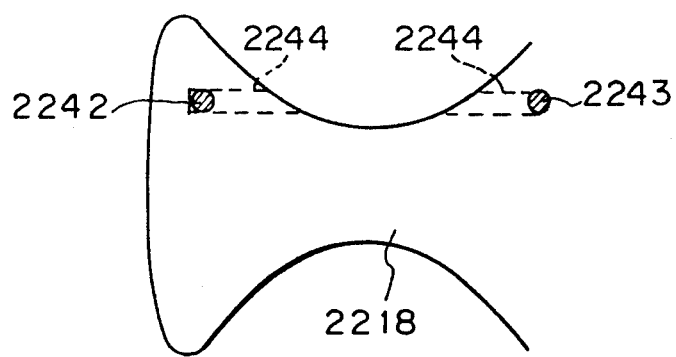
FIG. 44C is an expanded view of the portion shown in FIG. 44B.

FIG. 44A is a plane view showing the fingerprint input apparatus shown in FIGS. 37 and 38 providing optical sensors 2242 and 2243 for sensing whether or not the subject finger is moved to a predetermined location along the finger guide 2218. FIG. 44B is a side view showing the right side of the fingerprint input apparatus of FIG. 44A. FIG. 44C is an expanded view of the portion shown in FIG. 44B.

As shown in FIGS. 43A and 43B, and FIGS. 44A to 44C, the fingerprint input apparatuses according to these embodiments each includes a touch plate 2210, a supporting plate 2211, a finger guide 2218, a sensor 2213, an image pickup device (not shown), a lighting device (not shown), an image memory (not shown), and a CPU (not shown). These embodiments basically operate in a similar manner to the first embodiment of the seventh invention.

The finger guide 2218 provides on the upper and the lower surfaces grooves 2218a and 2218b formed along the moving direction of the finger F1 (toward the arrow shown in FIG. 44A). The groove 2218a is used for sliding the side of the subject finger F1 therethrough. The groove 2218b is used for sliding the side of the adjacent finger F2.

These grooves 2218a and 2218b are smoothed so as to suit to the forms of the fingers F1 and F2.

The finger guide 2218 further provides a cut-away 2218c allowing the fingerprint surface of the finger F1 to be seen at a predetermined input reading location.

The fingerprint input apparatus shown in FIGS. 43A and 43B provides a mechanical sensor 2241 on the groove 2218a side of the finger guide 2218 in a manner to locate the sensor 2241 at the position corresponding to the first joint, for example, of the subject finger F1. The fingers F1 and F2 clipping the finger guide 2218 push the mechanical sensor 2241 for turning on the sensor 2241. The mechanical sensor 2241 serves to sense the fingers F1 and F2 clipping the finger guide 2218 and send out a sensing signal to the CPU (not shown).

The fingerprint input apparatus shown in FIGS. 44A to 44C provides an optical sensor having a luminous part 2242 and a light-receptacle part 2243 on the groove 2218a side of the finger guide 2218. The optical sensor is located at the position corresponding to the first joint, for example of the finger F1. The luminous part 2242 is constructed to apply a ray of light to the light-receptacle part 2243. In case an optical path 2244 between the luminous part 2242 and the light-receptacle part 2243 is screened by the finger F1, the optical sensor senses the movement of the finger F1 along the grooves formed on the finger guide 2218 (with the fingers clipping the finger guide 2218) and sends out the sensing signal to the CPU (not shown).

Consider that the fingerprint input apparatus provides the optical sensor having the luminous part 2242 and the light-receptacle part 2243 for sensing the movement of the finger F1 along the groove of the finger guide 2218, the mechanical sensor 2241 (SW1) for sensing that the fingers F1 and F2 clip the finger guide 2218, and a sensor 2213 (SW2) for sensing that the finger tip is pushed to the touch plate 2210. In case the fingerprint pattern input is started when these sensors are all operated at a time, a message shown in the below-indicated table 1 is displayed depending on the ON or OFF state of each sensor so that an operator can grasp how those sensors are operated.

TABLE 1

| SW1 | SW2 | Message |
|---|---|---|
| OFF | OFF | "Insert your fingers clipping the finger guide" |
| OFF | ON | "Clip the finger guide with your fingers" |
| ON | OFF | "Insert your fingers as it stands" |
| ON | ON | "Currently in process, wait for a while" |

According to the present embodiment, therefore, the grooves 2218a and 2218b formed on the finger guide 2218 serve to define the distance between the fingerprint surface and the image pickup device (not shown). It results in allowing the image pickup device and the lighting device (not shown) to pick up a vivid image representing the fingerprint pattern, thereby reliably achieving the input of the fingerprint pattern.

The present embodiment is constructed to give to a user information about the operating state of the sensor 2213, the mechanical sensor 2241, or the optical sensor having the luminous part 2242 and the light-receptacle part 2243. Hence, the user can smoothly input the fingerprint pattern.

The above description about the present embodiment has concerned with the fingerprint input apparatus dedicated for a right hand. For constructing the apparatus dedicated for a left hand, it is possible to provide the touch plate, the finger guide, the sensor, the mechanical sensor, and the optical sensor having the luminous part and the light-receptacle part on the opposite side and locate the image pickup device and the lighting device at the opposite locations.

Figure 45:
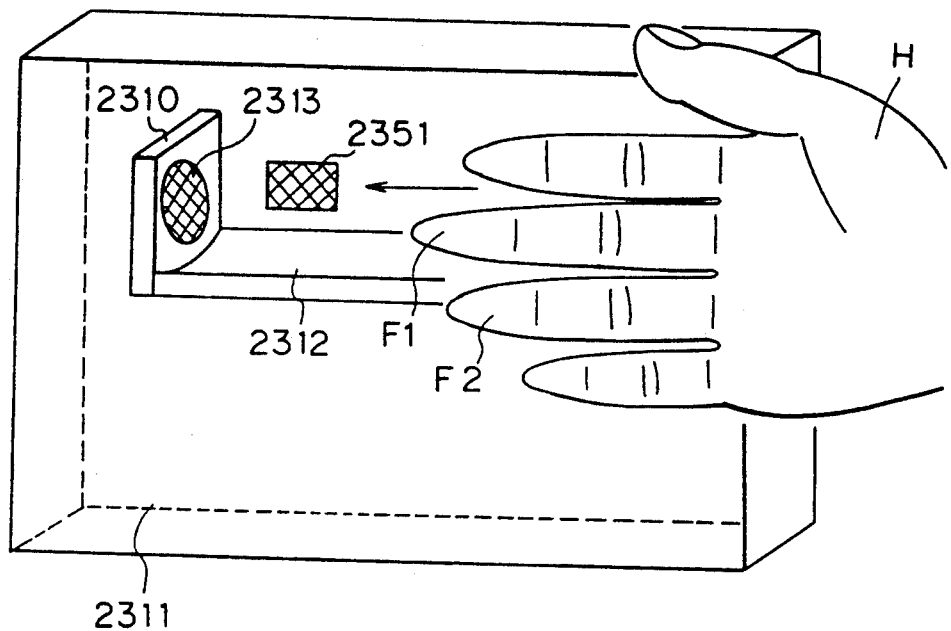
FIG. 45 is a schematic diagram showing the fingerprint input apparatus shown in FIG. 42 providing a mechanical sensor for sensing whether or not the perpendicular direction to the fingerprint surface.
Figure 46:
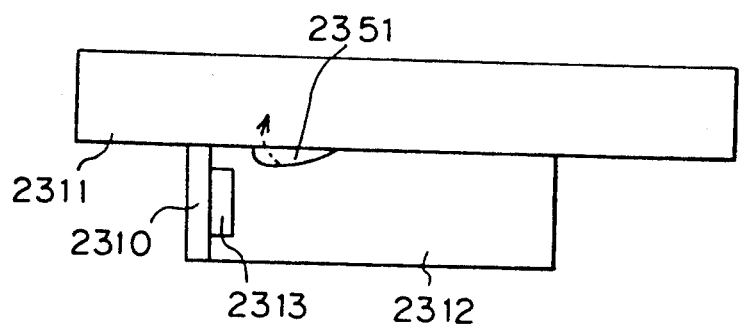
FIG. 46 is a top view showing the fingerprint input apparatus shown in FIG. 45.

FIG. 45 is a schematic view showing the fingerprint input apparatus shown in FIG. 36 providing a mechanical sensor 2351 for sensing the perpendicular position to the fingerprint surface when the subject finger F1 is moved along the finger guide 2312. FIG. 46 is a top view showing the apparatus shown in FIG. 45.

As shown in FIGS. 45 and 46, the fingerprint input apparatus according to the present invention includes a touch plate 2310, a supporting plate 2311, a finger guide 2312, a sensor 2313, a mechanical sensor 2351, an image pickup device (not shown), a lighting device (not shown), an image memory (not shown), and a CPU (not shown). The present embodiment basically operates in a manner to the first embodiment of the seventh invention shown in FIG. 36.

The sensor 2351 is provided on the supporting plate 2311 upward of the finger guide 2312 so that the sensor 2351 enables to sense the perpendicular position to the fingerprint surface when the finger F1 is moved along the finger guide 2312 and reaches a predetermined location. As shown in FIG. 46, the sensor 2351 is projected vertically in a normal state. When the finger F1 is moved along the finger guide 2312, the opposite surface of the finger F1 pushes the sensor 2351 so that the sensor 2351 is allowed to rotate toward the arrow shown by a broken line and be levelized with the supporting plate 2351.

When the sensor 2351 senses the finger F1, the sensor 2351 serves to send out a sensing signal to the CPU (not shown).

As shown in FIG. 45, the back of the hand H is moved toward the arrow along the supporting plate 2311 in a manner to allow the finger guide 2312 to be laid between the subject finger F1 and the adjacent finger F2. When the finger F1 reaches a predetermined input reading location, the sensors 2313 and 2351 serve to sense the finger F1.

When these sensors sense the finger F1, the sensors serve to send out the sensing signals to the CPU (not shown), respectively. In response to the sensing signals, the CPU activates the lighting device to light the fingerprint surface and sends out the imaging-start signal to the image pickup device. The light reflected on the fingerprint surface is picked up by the image pickup device. Then, the CPU controls the write of the fingerprint image picked up by the image pickup device into the image memory.

Since the fingerprint pattern is input in a non-contact manner, therefore, the present embodiment is capable of positively inputting a fingerprint pattern with no adverse effect of the residual fingerprint.

In addition, the present embodiment may has a capability of giving to the user information about how the sensors 2313 and 2351 are operated, resulting in allowing the user to smoothly input the fingerprint pattern. Those advantages make great contribution to enhancing the efficiency of collating and identifying the fingerprint.

The above description about the present embodiment has concerned with the fingerprint input apparatus dedicated for a right hand. For constructing the apparatus dedicated for a left hand, it is possible to provide the touch plate, the finger guide, the sensor corresponding to the sensor 2313, and the sensor corresponding to the sensor 2351 and locate the image pickup device and the lighting device at the opposite locations.

Many widely different embodiments of the present invention may be constructed without departing from the spirit and scope of the present invention. It should be understood that the present invention is not limited to the specific embodiments described in the specification, except as defined in the appended claims.

What is claimed is:

1. A fingerprint input apparatus comprising:
   a lightguide plate having a through hole on which a finger is placed;
   light sources for emitting rays of light;
   means for directing said rays of light into surfaces of said lightguide plate in a manner to keep such an angle of incidence as allowing said rays of light to be totally reflected within said lightguide plate, said lightguide plate being constructed to guide said rays of light to said through hole and to said finger; and
   an image pickup means located in opposition to said finger through said through hole therebetween, and said image pickup means being constructed to pick up light rays reflected from said finger placed on the through hole.

2. A fingerprint input apparatus according to claim 1, wherein said lightguide plate is made of a tabular glass plate and is formed to have a light propagating length of about 100 mm and a width of about 50 mm.

3. A fingerprint input apparatus according to claim 1, wherein said through hole has a slightly smaller diameter than an average finger diameter and is oval.

4. A fingerprint input apparatus according to claim 1, wherein two light sources included in said light sources are located as opposed to right and left end surfaces of said lightguide plate.

5. A fingerprint input apparatus according to claim 1, wherein said angle of incidence of the rays of light against said lightguide plate is adjusted to be slightly larger than a critical angle relevant to a total internal reflection.

6. A fingerprint input apparatus according to claim 1, wherein said light sources are constructed to emit parallel rays of light.

7. A fingerprint input apparatus according to claim 1, wherein said image pickup means is constructed to pick up said irregularly reflected light and to convert said irregularly reflected light into an electric signal.

8. A fingerprint input apparatus according to claim 1, wherein said lightguide plate includes two sides and an opposite surface to a light-incident surface of said lightguide plate, said two sides and said opposite surface being made of mirrors on which metal such as aluminum is vaporized.

9. A fingerprint input apparatus according to claim 1, wherein said through hole has a tapered inner wall progressively spread downwardly.

10. A fingerprint input apparatus according to claim 1, wherein said through hole has a straight inner wall.

11. A fingerprint input apparatus according to claim 1, wherein said through hole has a tapered inner wall progressively curved in a downward manner.

12. A fingerprint input apparatus comprising:
a light source for emitting a ray of light;
a lightguide plate having a plurality of surfaces and a predetermined contact location on one of the surfaces whereat a finger can be in contact with said lightguide plate;
means for directing the ray of light into at least one surface of said lightguide plate in a manner to keep such an angle of incidence as allowing the ray of light to be totally reflected within said lightguide plate, said lightguide plate being constructed to totally reflect the light ray at least twice in the plate and to guide the ray of light within said lightguide plate into said predetermined contact location; and
an image pickup means located near said predetermined contact location of said lightguide plate and outside a surface which is opposite to the surface having the predetermined contact location, said image pickup means being constructed to pick up light irregularly reflected from a fingerprint surface of the finger contacted with said predetermined contact location.

13. A fingerprint input apparatus according to claim 12, wherein said lightguide plate is made of a tabular glass plate and is formed to have a light propagating length of about 100 mm and a width of about 30 mm to 40 mm.

14. A fingerprint input apparatus according to claim 12, wherein said means for directing the ray of light into at least one surface of said lightguide plate includes a prism having an isosceles triangle in section.

15. A fingerprint input apparatus according to claim 12, wherein said image pickup means is constructed to pick up the irregularly reflected light and to convert the irregularly reflected light into an electric signal.

16. A fingerprint input apparatus comprising:
at least one light source for emitting a ray of light;
a lightguide plate having a plurality of surfaces including a light-incident surface whereupon the ray of light is incident, a surface opposite the light-incident surface, a surface having a predetermined contact location provided thereon, and a surface opposite the surface having the predetermined contact location, the predetermined contact location being provided for a finger to be in contact therewith, the lightguide plate being constructed to totally reflect the light ray at least twice in the plate and to guide the ray of light within said lightguide plate into said predetermined contact location, the surface opposite the light-incident surface, the surface having the predetermined contact location provided thereon, and the surface opposite the surface having the predetermined contact location being formed by mirrors; and
an image pickup means located near said predetermined contact location of said lightguide plate and outside the surface which is opposite the surface having the predetermined contact location, said image pickup means being constructed to pick up light irregularly reflected from a fingerprint surface of the finger contacted with said predetermined contact location.

17. A fingerprint input apparatus according to claim 16, wherein said lightguide plate is made of a tabular glass plate and is formed to have a light propagating length of about 100 mm and a width of about 30 mm to 40 mm.

18. A fingerprint input apparatus according to claim 16, wherein said image pickup means is constructed to pick up the irregularly reflected light and to convert the irregularly reflected light into an electric signal.

19. A fingerprint input apparatus according to claim 16, wherein a surface of said lightguide plate lit by said at least one light source is formed to keep a right angle of incidence of the ray of light emitted by said at least one light source.

20. A fingerprint input apparatus according to claim 16, wherein two light sources included in said at least one light source are constructed to respectively apply rays of light to both surfaces opposite to each other of said lightguide plate.

21. A fingerprint input apparatus according to claim 16, wherein said mirrors are made of a reflective metal.

22. A fingerprint input apparatus according to claim 21, wherein said mirrors are made of aluminum.

* * * * *